United States Patent
Piazza et al.

(10) Patent No.: US 11,484,537 B2
(45) Date of Patent: Nov. 1, 2022

(54) 3β-(4-METHOXYBENZYLOXY)PREGN-5-EN-20-ONE FOR USE IN THE TREATMENT OF CANNABINOIDS-RELATED DISORDERS

(71) Applicants: AELIS FARMA, Bordeaux (FR); INSERM (Institut National de la Santé et de la Recherche Médicale), Paris (FR); UNIVERSITE DE BORDEAUX, Bordeaux (FR)

(72) Inventors: Pier Vincenzo Piazza, Bordeaux (FR); Sandy Fabre, Bordeaux (FR); Mathilde Metna, Bordeaux (FR); Stéphanie Monlezun, Bordeaux (FR); Arnau Busquet-Garcia, Bordeaux (FR); Daniela Cota, Bordeaux (FR); Giovanni Marsicano, Bordeaux (FR); Jean-Michel Revest, Bordeaux (FR); Monique Vallée, Bordeaux (FR)

(73) Assignees: AELIS FARMA, Bordeaux (FR); INSERM (Institut National de la Santé et de la Recherche Médicale), Paris (FR); UNIVERSITE DE BORDEAUX, Bordeaux (FR)

( * ) Notice: Subject to any disclaimer, the term of this patent is extended or adjusted under 35 U.S.C. 154(b) by 0 days.

(21) Appl. No.: 16/968,237

(22) PCT Filed: Feb. 20, 2019

(86) PCT No.: PCT/EP2019/054217
§ 371 (c)(1),
(2) Date: Aug. 7, 2020

(87) PCT Pub. No.: WO2019/162328
PCT Pub. Date: Aug. 29, 2019

(65) Prior Publication Data
US 2021/0030768 A1 Feb. 4, 2021

(30) Foreign Application Priority Data
Feb. 20, 2018 (EP) .................................... 18305177

(51) Int. Cl.
*A61K 31/57* (2006.01)
*A61P 25/30* (2006.01)

(52) U.S. Cl.
CPC .............. *A61K 31/57* (2013.01); *A61P 25/30* (2018.01)

(58) Field of Classification Search
CPC ................................ A61K 31/57; A61P 25/30
See application file for complete search history.

(56) References Cited

U.S. PATENT DOCUMENTS 10,259,839 B2 * 4/2019 Piazza ..................... A61P 25/04
2015/0284423 A1 * 10/2015 Piazza ..................... A61P 15/08
514/182

FOREIGN PATENT DOCUMENTS

WO 2012/160006 A1 11/2012
WO 2014/083068 A1 6/2014

OTHER PUBLICATIONS

Vallée et al., "Pregnenolone can protect the brain from cannabis intoxication," Science Jan. 3, 2014;343(6166):94-98. PMID: 24385629. (Year: 2014).*
Tait et al., "A systematic review of adverse events arising from the use of synthetic cannabinoids and their associated treatment," Clin. Toxicol. (Phila). 2016;54(1):1-13. PMID: 26567470. (Year: 2016).*
Busquets-Garcia et al., "Pregnenolone blocks cannabinoid-induced acute psychotic-like states in mice," Molecular Psychiatry. (2017), 22(11):1594-1603.
International Search Report and Written Opinion issued in the International Application No. PCT/EP2019/054217 dated Aug. 5, 2019.
Keown, A. (Dec. 5, 2019) "Sage's MDD Treatment Fails to Distinguish Itself From Placebo in Late-Stage Trial," BioSpace. (2019), https://www.biospace.com/article/sage-plunges-after-phase-iii-setback-in-major-depressive-disorder/ (accessed 5:03 PM, May 12, 2022).
Althaus A. L., et al., "Preclinical characterization of zuranolone (SAGE-217), a selective neuroactive steroid GABAA receptor positive allosteric modulator," Neuropharmacology (2020) 181:108333.
Declaration under 37 C.F.R 1.132 filed Jun. 28, 2018 in U.S. Appl. No. 14/443,778 (now U.S. Pat. No. 10,259,839; "Piazza 1").

(Continued)

*Primary Examiner* — Theodore R. Howell
(74) *Attorney, Agent, or Firm* — Hogan Lovells US LLP

(57) ABSTRACT

The present invention generally relates to a specific pregnenolone derivative for its use for the treatment of a Cannabinoids-Related Disorder. More particularly, the invention relates to a compound of Formula (I)

Formula (I)

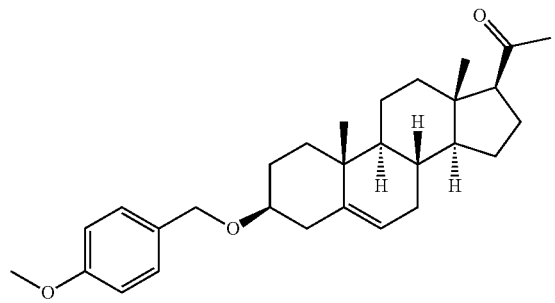

for its use in the treatment of a Cannabinoids-Related Disorder. Indeed, the compound of the invention is in vivo very potent in inhibiting the effects of THC, and is able to inhibit both unconditioned and conditioned effects of THC including THC self-administration and reinstatement in THC seeking in non-human primates.

19 Claims, 10 Drawing Sheets

(56) References Cited

OTHER PUBLICATIONS

"Cannabis-Related Disorders," Diagnostic and Statistical Manual of Mental Disorders DSM-5, 5th Edition (2013) 509-519.
Howlett, A.C., "Cannabinoid Receptor Signaling," Neuroscience/Drug Abuse Research Program (2005) 168:53-79.
Nagai, Hiroshi, et al., "Antipsychotics improve Δ9-tetrahydrocannabinol-induced impairment of the prepulse inhibition of the startle reflex in mice," Pharmacology, Biochemistry and Behavior (2006)84:330-336.
Puighermanal, Emma, et al., "Cannabinoid modulation of hippocampal long-term memory is mediated by mTOR signaling," Nature Neuroscience (2009) 12(9):1152-1160.
Wiley, Jenny, "Age-dependent differences in sensitivity and sensitization to cannabinoids and 'club drugs' in mail adolescent and adult rats," Addiction Biology (2007) 13:277-286.
Marx, C. E. et al, Neuropsychopharmacology (2009) 34(8):1885-1903.

* cited by examiner

| Class | Synthetics cannabinoids | | |
|---|---|---|---|
| Dibenzoypyrans (Classical cannabinoids) | THC  | HU-210  | |
| Naphtoylindoles | JWH-018  | JWH-073  | AM-2201  |
| Cyclohexylphenols | CP-47,497  | CP-55,940  | |
| Phenylacetylindoles | JWH-250  | RCS-4  | |
| Tetramethylcyclo-propanoylindoles | XLR-11  | | |
| Indazole-3-carboxamides | AB-CHIMINACA  | AB-FUBINACA  | |
| Aminoalkylindoles | WIN 55,212-2  | | |

| Toxicity in GLP Studies | CB$_1$ antagonist (Rimonabant) | | | 3$p$MBP | | |
|---|---|---|---|---|---|---|
| | Effect | ED100 (mg/kg) | Safety Index | Effect | Highest dose tested (mg/kg) | Safety Index |
| Acute Toxicity | (ip) Rodent | | | (oral) Rat | | |
| Clinical Toxicity: decubitus, prostration, decreased activity, weakness, piloerection, soiled urogenital area, nasal discharge | Yes | 60 | 6 | No | 36 | >7200 |
| CNS Toxicity: locomotor hyperactivity followed by sedation | Yes | 3 | 0.3 | No | 36 | >7200 |
| Clonic Convulsion | Yes | 60 | 6 | No | 36 | >7200 |
| Maximum non lethal dose | Yes | 60 | 6 | No | 36 | >7200 |
| Repeated dose toxicity (oral) RAT | | | | | | |
| Clinical Toxicity: thinness, dried blood on the muzzle, swelling around eyes and red exudates/lacrimation from the eyes, soiled urogenital area, piloerection, dehydration, hypotonia, loss of balance | Yes | 6 (Females) 40 (Males) | 0.6 (Females) 4 (Males) | No | 36 | >7200 |
| CNS Toxicity: Hyperexcitability: hyperesthesia, tactile hyperesthesia or hypersensitivity to touch, excessive scratching, hyperexcitability, hyperactivity, hypermotility, aggressiveness and combative behavior | Yes | 30 | 3 | No | 36 | >7200 |
| Clonic convulsion | Yes | 6 (Females) 40 (Males) | 0.6 (Females) 4 (Males) | No | 36 | >7200 |
| Liver Toxicity: Focal hepatocellular necrosis, steatosis, Increase in liver weight and size, hypertrophy of centrilobular hepatocytes with ground-glass appearance of the cytoplasm and hyperplasia of the smooth endoplasmic reticulum. | Yes | 40 | 4 | No | 36 | >7200 |
| Mortality | Yes | 60 (Females) 120 (Males) | 6 (Females) 12 (Males) | No | 36 | >7200 |
| Repeated dose toxicity (oral) dog | | | | | | |
| Clinical Signs: ptyalism; tremors, red conjunctiva, ataxia, hypomotility, | Yes | 10-15 | ND | No | 36 | ND |
| CNS Signs: aggressiveness and startling movements | Yes | 15 | ND | No | 36 | ND |

FIG. 12

3β-(4-METHOXYBENZYLOXY)PREGN-5-EN-20-ONE FOR USE IN THE TREATMENT OF CANNABINOIDS-RELATED DISORDERS

RELATED APPLICATIONS

This application is a U.S. National Stage application under 35 U.S.C. 371 of PCT/EP2019/054217, having an international filing date of Feb. 20, 2019, which designated the United States, which PCT application claims the benefit of European Application No. 18305177.0 filed on Feb. 20, 2018, each of which are incorporated herein by reference in their entireties.

FIELD OF THE INVENTION

The present invention relates to the field of substance use disorders, and in particular to the field of Cannabinoids-Related Disorders. It relates to a particular pregnenolone derivative, "3β-(4-methoxybenzyloxy)pregn-5-en-20-one", that cannot be metabolized in vivo into active pregnenolone metabolites and its use for the treatment of Cannabinoids-Related Disorders.

BACKGROUND OF THE INVENTION

Cannabinoids preparation containing synthetic CB1 agonists or extract derived from the plant *Cannabis sativa*, are the most widely used illicit psychoactive substances in the United States and in European countries.

The consequences of cannabinoids use especially but not limited to the most prone population (14-25 years of age) are extremely serious, and may include addiction, altered brain development with reduced IQ, precipitation of psychiatric disease including but not limited to schizophrenia and depression, entry of the subjects in Emergency Room for different intoxication syndromes, poorer educational outcomes, cognitive impairment, lower income, greater welfare dependence, unemployment and lower relationship and life satisfaction (Substance Abuse and Mental Health Services Administration (2013). *Results from the* 2013 *National Survey on Drug Use and Health: Summary of National Findings*; Cerdá et al., 2012; Volkow et al., 2014; Hall et al., 2009).

In the United States, the 12-month prevalence of cannabinoids addiction as defined in one of the most used diagnostic manuals as *cannabis* use disorder is approximately 3.4% among 12- to 17-year-olds and 1.5% among adults age 18 years and older. Rates of cannabinoids use disorder are greater among adult males (2.2%) than among adult females (0.8%) and among 12- to 17-year-old males (3.8%) than among 12- to 17-year-old females (3.0%). Twelve-month prevalence rates of cannabinoids use disorders among adults decrease with age, with rates highest among 18- to 29-year-olds (4.4%) and lowest among individuals aged 65 years and older (0.01%). Ethnic and racial differences in prevalence are moderate. Cannabinoids use is also responsible in the US of 450 000 entry in emergency room per year (DAWN report, 2013). Several types of symptoms are observed in these patients. The most commons are: a. profound anxiety state that approximates a panic attack: b. psychosis, delirium and a profoundly disorganized behavior; c. a hyperemesis syndrome; d. catatonic behavior (Adams et al 2017, Khan et al., 2016).

Finally, cannabinoids use is increasing and will only further escalate with legalization of recreational and medical *cannabis* use in western countries, with prevalence greater than 30% in the US and most European countries for individuals between 16 and 24 years of age. Approximately 9% of those who use *cannabis* will become addicted. The number goes up to about 1 in 6 among those who start using marijuana as teenagers and to 25 to 50% among those who smoke marijuana daily.

Cannabinoids-Related Disorders result notably from the activation of the CB1 receptor by $\Delta^9$-tetrahydrocannabinol (THC), the primary psychoactive ingredient of *cannabis* or by any other synthetic compound, like synthetic cannabinoids.

Methods aimed at blocking the activity of the CB1 through inhibition of the orthosteric binding site, the site at which the endogenous ligands bind to activate the receptor, have been developed and submitted for clinical trials for the reduction of body weight. One of these compounds, rimonabant, has even been put on the market with the brand name Acomplia®. Unfortunately, available orthosteric antagonists such as rimonabant inhibit the entire activity of the receptor and also act as inverse agonists of the CB1 receptor, i.e. they not only inhibit the activation of the CB1, but also the basal activity of the receptor in the absence of the endogenous ligand. Because of this inverse agonist action and the total inhibition of the receptor activity, available methods based on the administration of orthosteric CB1 antagonists also have a series of serious adverse effects. Because of these adverse effects, commercialization of Acomplia® has been suspended and the development of other methods for inhibiting the orthosteric site of the CB1 has been stopped.

Orthosteric CB1 antagonists and in particular Acomplia® have the following known adverse effects that make them unpractical tools to treat Cannabinoids-Related Disorders:
1. They reduce food intake which indicates a general disruption of the reward system;
2. They induce anxiety-related behavior in animals and anxiety in humans;
3. They induce depression-related behaviors in animals and depression in humans;
4. They increase glucocorticoid secretion inducing an impairment of the subject hormonal status. In particular an increase in glucocorticoid can increase the activity of the dopaminergic system which mediated the rewarding effects of drugs of abuse including cannabinoids. An increased glucocorticoid secretion can then result in an increased sensitivity to the rewarding effects of cannabinoids which can counteract the therapeutic effects of CB1 inhibitor on cannabinoids related disorders;
5. They precipitate withdrawal in THC dependent animals;
6. They induce convulsions and a general behavioral and clinical impairment in GLP safety pharmacology and toxicology studies;
7. They have hepatotoxic effects.

It has been recently discovered that when the CB1 receptor is over-activated by synthetic cannabinoids or by very high doses of THC, quite higher than the dosed of THC used by *cannabis* abusers, the concentration of the steroid hormone pregnenolone increases (3000%) in the brain. Pregnenolone then binds to a specific site on the CB1 receptor, distinct from that bound by CB1 agonists such as THC, and acts as an endogenous signaling specific inhibitor of the CB1 receptor (eCB1-SSi). Thus, pregnenolone selectively inhibits CB1-induced activation of the MAPK (Mitogen-Activated Protein Kinase) pathway but not CB1-induced inhibition of Adenylate cyclase. Despite this restricted molecular action, when pregnenolone is administered prior to the exposure to THC, it inhibits most of THC-mediated behavioral effects in rodents (Vallée et al., 2014).

Busquets-Garcia et al. also demonstrate that pregnenolone can block the full range of unconditioned effect of THC that are related to psychotic-like symptoms that are observed after cannabinoids use in humans. Thereby suggesting that drugs mimicking pregnenolone activity could be used to treat cannabinoids-induced acute psychotic-like states (CIAPS) (Busquets-Garcia et al., 2017).

For these reasons, pregnenolone seems to be a promising treatment of Cannabinoids-Related Disorders.

However, pregnenolone cannot be used as a pharmacological treatment because it is poorly available, has a very short half-life and is converted in downstream to active steroids.

In WO2012/160006, three derivatives of pregnenolone, namely 3-Fluoropregnenolone, 17-methylpregnenolone, 3-fluoro-17-methylpregnenolone, have been tested in rat or mice after stimulation with THC and/or after food deprivation. These compounds were able to inhibit the effects of CB1 activation on food intake.

Other compounds, and notably 3β-benzyloxypregnenolone were tested for their ability to inhibit: i. effects of the THC-induced cannabinoid tetrad (decrease in body temperature and in locomotor activity); ii. THC-induced increase in food intake, a typical effect of CB1 activation; iii. the increase in TNFalpha induced by LPS, another effect typical of CB1 antagonists.

WO2014/083068 discloses "3β-(4-methoxybenzyloxy) pregn-5-en-20-one" and its use for inhibiting CB1 receptor, however in a very general way. There is no mention of inhibiting the activation of CB1 caused by THC in particular.

However, there are no approved pharmacological treatments for Cannabinoids-Related Disorders, which is consequently an important unmet medical need.

Accordingly, there remains a need for the treatment of Cannabinoids-Related Disorders.

Developing a treatment of Cannabinoids-Related Disorders based on a signaling specific inhibition of the CB1 receptor that can be used in humans present several challenges. Thus, such compound should show concomitantly all the following characteristics:
1. It should inhibit the activity of the CB1 receptor in a selective and signaling specific manner.
2. It should inhibit a large spectrum of unconditioned and conditioned behavioral effects of CB1 agonists in order to be of use for treating the different Cannabinoids-Related Disorders. This a particular challenge for a signaling specific inhibitor. Since this compound modifies only certain cellular effects of the activation of the CB1 by an agonist. Consequently, it is impossible to predict which, among the different behavioral effects of cannabinoids, will be modified by a signaling specific inhibitor.
3. It should be devoid of the known adverse effects of CB1 inhibitors. In particular it should not induce: a. a decrease in food-intake; b. an increase in anxiety- and depression-related behaviors; c. an increase in glucocorticoid secretion; d. withdrawal in THC dependent animals; e. convulsion and an impairment of central nervous system related clinical signs; f. hepatotoxicity.
4. It should not have unspecific behavioral effects including but not limited to sedation, excitability, altered spontaneous behavior that can interfere with its therapeutic effects.
5. It should be well absorbed, stable and not transformed in vivo, in significant quantities of downstream metabolites that can have adverse effects, including but not limited to active steroids.
6. It should access the brain that it is the target organ of a therapeutic tool aimed to treat Cannabinoids-Related Disorders.
7. It should not modify the major body metabolic enzyme and transporters that can induce modifications on the level or activity of endogenous molecules or exogenous therapeutic drugs.
8. It should have a good therapeutic index (the ration between the active dose and the dose showing adverse effects). An acceptable therapeutic index is generally considered to be at least 10.

For none of the signaling specific inhibitor and other antagonists of the CB1 receptors described above or in previous available knowledge all the above mentioned features have been described. More generally practically no compound used to treat behavioral disorders has all these characteristics. Thus, the three major classes of psychoactive drugs, anxiolytic, antidepressants and neuroleptics induce behavioral adverse effects in the range of the therapeutic doses. For example: a. Anxiolytic drugs induce sleepiness, decrease alertness and impair memory; b. Antidepressant induces excitability, insomnia and a decrease in libido; c. Neuroleptic induces hormonal disruption, sedation, dyskinesia and involuntary movement.

Consequently, a compound that has all the characteristic described in points 1 to 8 would not only be a major innovation for a drug designed to treat Cannabinoids-Related Disorders but also a major innovation for the entire field of psychoactive drugs aimed to treat behavioral disorders.

SUMMARY OF THE INVENTION

The present invention generally relates to a specific pregnenolone derivative for its use for the treatment of a Cannabinoids-Related Disorder.

More particularly, the invention relates to a compound of Formula (I)

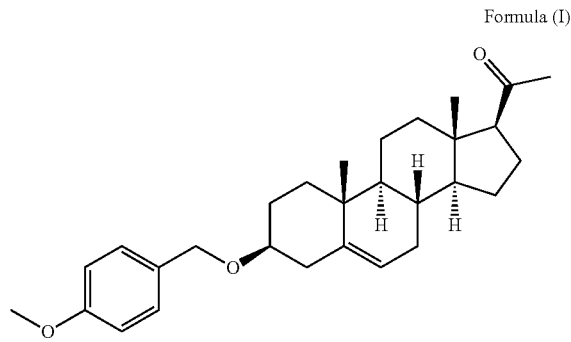

Formula (I)

for its use in the treatment of a Cannabinoids-Related Disorder.

Indeed, the compound of the invention has the unique characteristic of having all the below described properties that make it a very innovative therapeutic tool to treat Cannabinoids-Related Disorders.
1. It inhibits selectively the activity of the CB1 receptor in a signaling specific manner;
2. It is very potent in inhibiting a large spectrum of unconditioned and conditioned behavioral effects of CB1 agonists and can consequently be of use for the treatment of Cannabinoids-Related Disorders;

3. It is devoid of the known adverse effects of CB1 inhibitors and antagonists. In particular it does not: a. decrease food intake; b. increase anxiety- and depression-related behaviors; c. increase glucocorticoid secretion; d. precipitate withdrawal in THC dependent animals; e. induce convulsion and impairment and central nervous system related clinical signs; f. induce liver toxicity in GLP studies.
4. It has not unspecific behavioral effects such as sedation, excitability, altered spontaneous behavior that could interfere with its therapeutic action.
5. It is well absorbed, stable and not transformed in significant quantities in downstream metabolites.
6. It accesses the brain.
7. It does not modify the major body metabolic enzymes and transporters.
8. It has an excellent therapeutic index >7200.

BRIEF DESCRIPTION OF THE DRAWINGS

FIG. 2A: Effect of 3pMBP (0, 1, 10 and 100 nM) on THC-induced phosphorylation of MAPK. P-MAPK/CoxIV ratio from HEK293 cells stably transfected with hCB1.

FIG. 2B: Effect of 3pMBP (0, 1, 10 and 100 nM) on THC-induced phosphorylation of MAPK. P-MAPK/MAPK ratio from HEK293 cells transiently transfected with hCB1.

FIG. 2C: Effect of 3pMBP (1 nM, 10 nM, 100 nM and 1 μM) on THC-induced decrease of cAMP levels in CHO cells stably transfected with hCB1. NT=Not Treated, i.e. cells that received both the vehicle of 3pMBP and of THC.

FIG. 2D: Effect of 3pMBP (0, 1, 10 and 100 nM) on THC-induced inhibition of cellular respiration in HEK293 cells transiently transfected with hCB1.

*$p<0.001$; $p<0.01$; *$p<0.05$, groups treated with THC vs group treated with the vehicle of THC; ###$p<0.001$; ##$p<0.01$; #$p<0.05$, groups treated with 3pMBP+THC vs group treated with the vehicle of 3pMBP (0 nM)+THC. (A, B Tukey test, D. Dunnett test).

Figure 3:
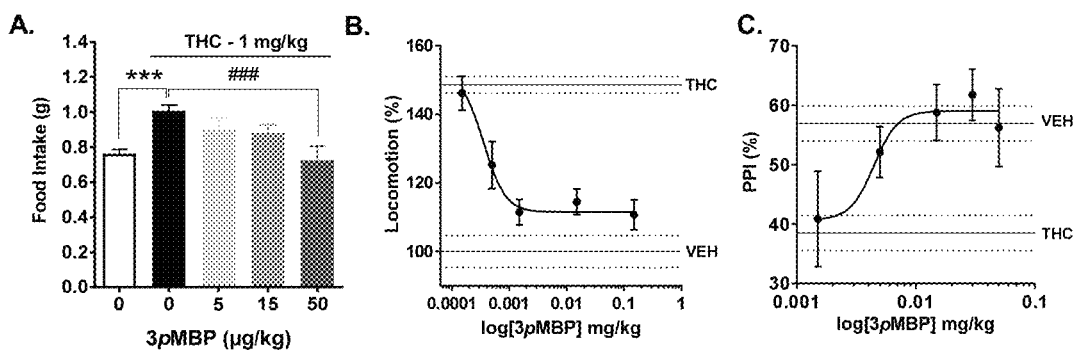

FIG. 3: Effects of 3pMBP on THC-induced hyperphagia, psychomotor stimulation and prepulse inhibition impairment:

FIG. 3A: 3pMBP (per os) dose dependently prevents in mice the increase in food intake induced by TH1C (1 mg/kg; ip).

***$p<0.001$, THC vs vehicle of THC; ###$p<0.001$, 3pMBP+THC vs Vehicle of 3pMBP (0 μg/kg)+THC (Dunnett test).

FIG. 3B: 3pMBP (per os) dose dependently prevents in mice the increase in locomotion induced by THC (0.3 mg/kg; ip).

Continuous black lines correspond to means; dotted black lines correspond to SEM values of groups treated with the vehicle of THC (VEH) or with THC in the absence of 3pMBP. Black circles, mean±SEM values of groups treated with 3pMBP and THC.

$p>0.05$, 3pMBP (0.00015 mg/kg)+THC vs Vehicle of 3pMBP+THC, $p<0.01$, 3pMBP (0.0005 mg/kg)+THC vs Vehicle of 3pMBP+THC, $p<0.001$, 3pMBP (0.0015 mg/kg)+THC, 3pMBP (0.015 mg/kg)+THC and 3pMBP (0.15 mg/kg)+THC vs Vehicle of 3pMBP+THC.

(Dunnett test after one-way ANOVA, $p<0.001$).

FIG. 3C: 3pMBP (per os) dose dependently prevents in mice the impairment of prepulse (82 dB) inhibition (PPI) induced by THC (10 mg/kg; ip).

Continuous black lines correspond to means; dotted black lines correspond to SEM values of groups treated with the vehicle of THC (VEH) or with THC in the absence of 3pMBP. Black circles, mean±SEM values of groups treated with 3pMBP and THC.

$p>0.05$, 3pMBP (0.0015 mg/kg)+THC and 3pMBP (0.005 mg/kg)+THC vs Vehicle of 3pMBP+THC, $p<0.05$, 3pMBP (0.015 mg/kg)+THC and 3pMBP (0.05 mg/kg)+THC vs Vehicle of 3pMBP+THC, $p<0.01$, 3pMBP (0.03 mg/kg)+THC vs Vehicle of 3pMBP+THC (Dunnett test after one-way ANOVA, $p<0.001$).

Figure 4:
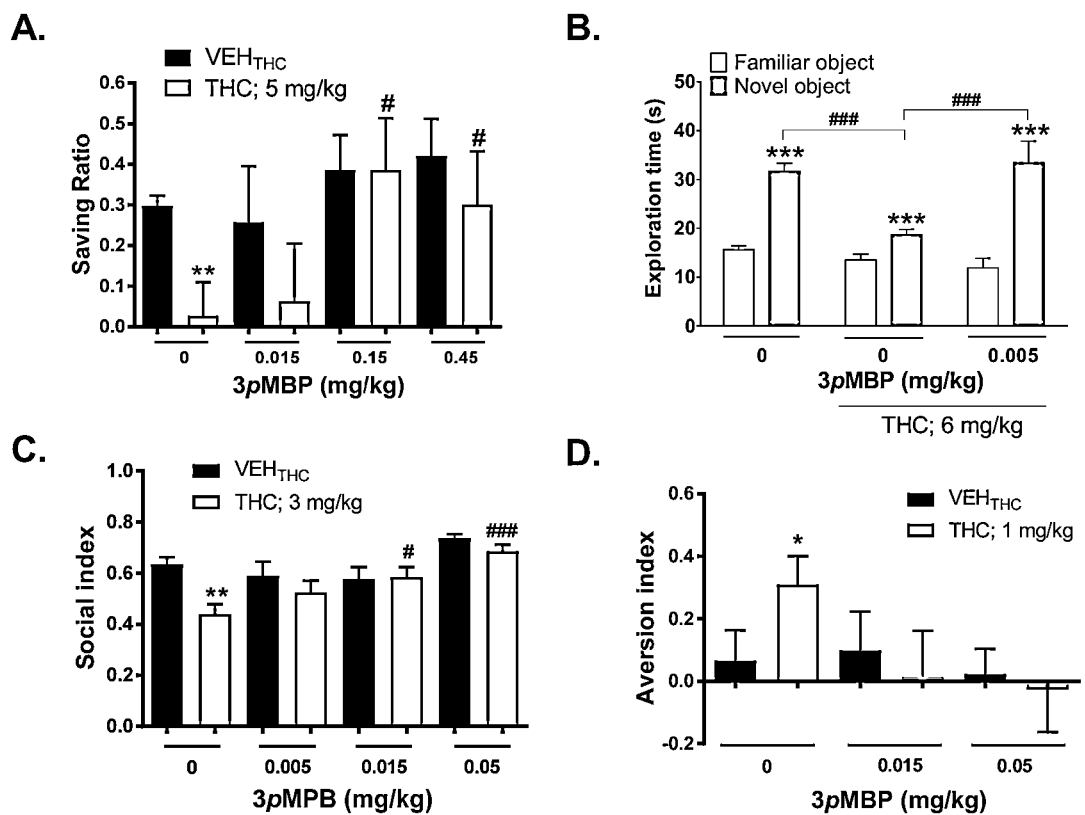

FIG. 4: Effects of 3pMBP on THC-induced impairments of working memory, object recognition, social interaction and reality testing.

FIG. 4A: 3pMBP (per os) dose dependently prevents in mice the impairment of working memory induced by THC (5 mg/kg) in the water maze.

**$p<0.01$, THC vs Vehicle of THC (VEH$_{THC}$; Dunnett test).

$p<0.05$, 3pMBP+THC vs Vehicle of 3pMBP (0 mg/kg)+THC (Dunnett test).

FIG. 4B: 3pMBP (per os) prevents in mice the impairment of object recognition induced by THC (6 mg/kg).

***$p<0.001$, Familiar vs Novel object (Sidak test).

$p<0.001$, exploration time of the novel object: Vehicle 3pMBP (0 mg/kg)+THC vs Vehicle 3pMBP (0 mg/kg) and no THC or vs 3pMBP+THC (Sidak test).

FIG. 4C: 3pMBP (per os) dose dependently prevents in mice the impairment of social interaction induced by THC (3 mg/kg).

**$p<0.01$, THC vs Vehicle of THC (VEH$_{THC}$; Dunnett test).

$p<0.001$; #$p<0.05$, 3pMBP+THC vs Vehicle of 3pMBP (0 mg/kg)+THC (Dunnett test).

FIG. 4D: 3pMBP (per os) dose dependently prevents in mice the impairment of reality testing induced by THC (1 mg/kg).

*$p<0.05$, THC vs Vehicle of THC (VEH$_{THC}$; unpaired t-test).

Figure 5:
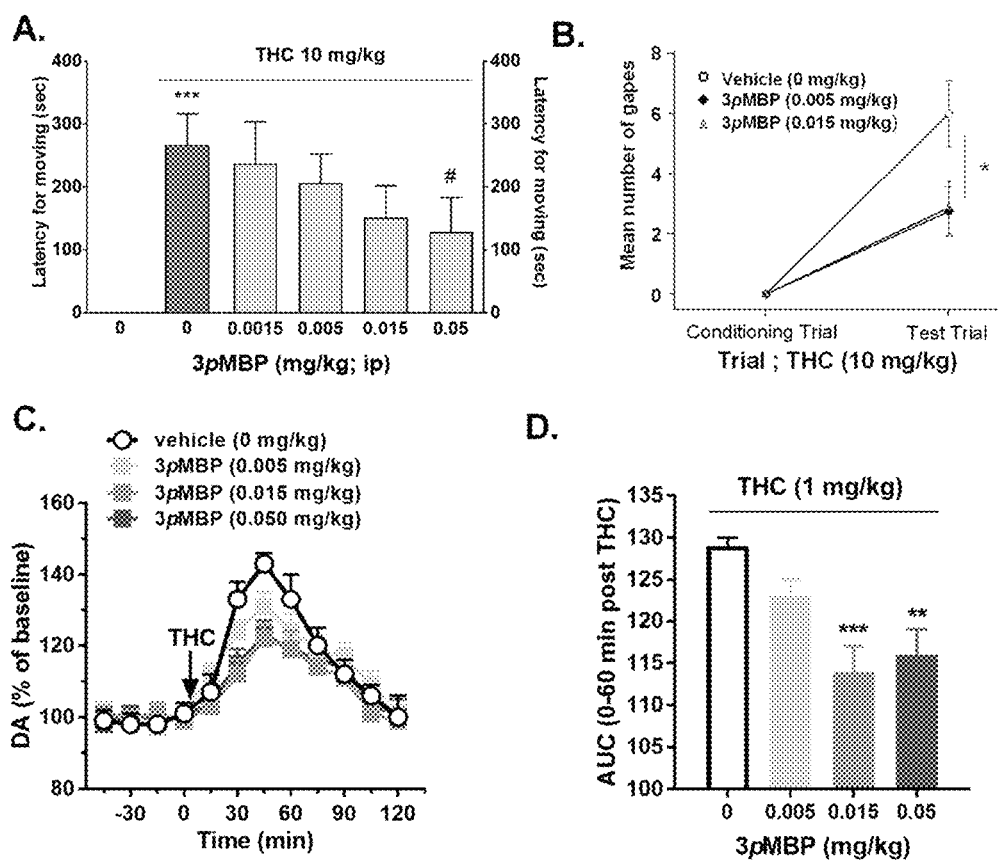

FIG. 5: Effects of 3pMBP on THC-induced catalepsy, conditioned gaping and dopamine release in the nucleus accumbens.

FIG. 5A: 3pMBP (per os) dose dependently reduces in mice the catalepsy induced by THC (10 mg/kg).

***$p<0.001$, THC vs Vehicle THC (Mann-Whitney test).

$p<0.05$, 3pMBP+THC vs Vehicle of 3pMBP (0 mg/kg)+THC (Mann-Whitney test).

FIG. 5B: 3pMBP (per os) prevents in mice the conditioned gaping induced by THC (10 mg/kg). Mean±SEM number of gapes elicited by THC-paired saccharin solution when pre-treated with 3pMBP (0.005 and 0.015 mg/kg) or Vehicle of 3pMBP (0 mg/kg) during conditioning and test trial.

*$p<0.05$, 3pMBP+THC vs Vehicle of 3pMBP (0 mg/kg)+THC (one-way ANOVA, main effect of 3pMBP administration).

FIG. 5C: 3pMBP inhibits the increase in dopamine outflow over time in the nucleus accumbens of rats treated with THC (1 mg/kg). Black arrow, THC injection time.

FIG. 5D: 3pMBP decreases the mean areas under the curve (AUC, calculated from times "0" to 60 min for each group) of dopamine outflow in the nucleus accumbens of rats treated with THC (1 mg/kg).

*$p<0.001$; $p<0.01$, 3pMBP+THC vs Vehicle of 3pMBP (0 mg/kg)+THC (Dunnett test).

Figure 6:
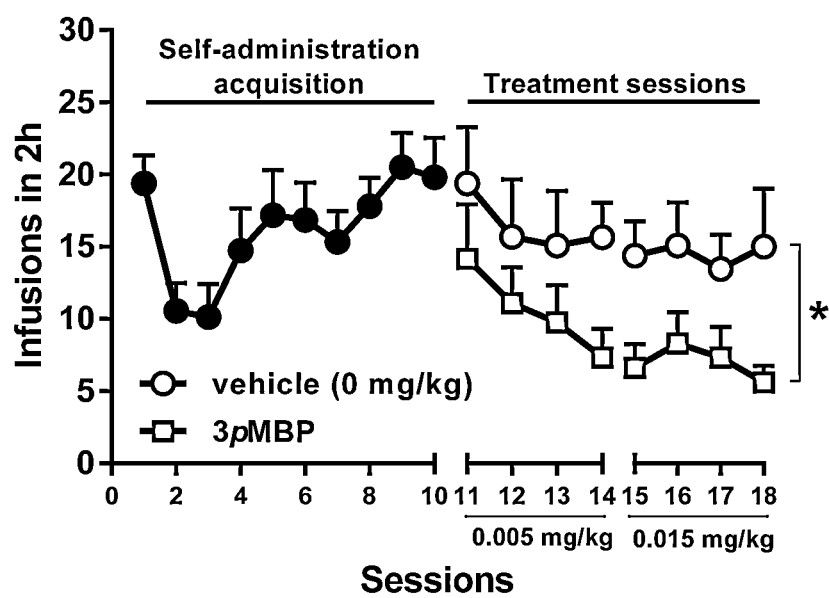

FIG. 6: Effects of 3pMBP on intravenous self-administration of WIN 55,212-2 in mice. 3pMBP (per os) decreases WIN 55-512,2 (0.0125 mg/kg/infusion; iv) self-administration in mice. Number of infusions during the acquisition of self-administration (first 10 sessions, black-filled circles) and during self-administration sessions with 3pMBP (0.005 mg/kg, sessions 11-14 and 0.015 mg/kg, sessions 15-18; grey squares) or with Vehicle of 3pMBP (0 mg/kg, white-filled circles).

*$p<0.05$, 3pMBP (0.015 mg/kg)-treated group vs Vehicle (0 mg/kg) (two-way ANOVA, main effect of 3pMBP administration).

Figure 7:
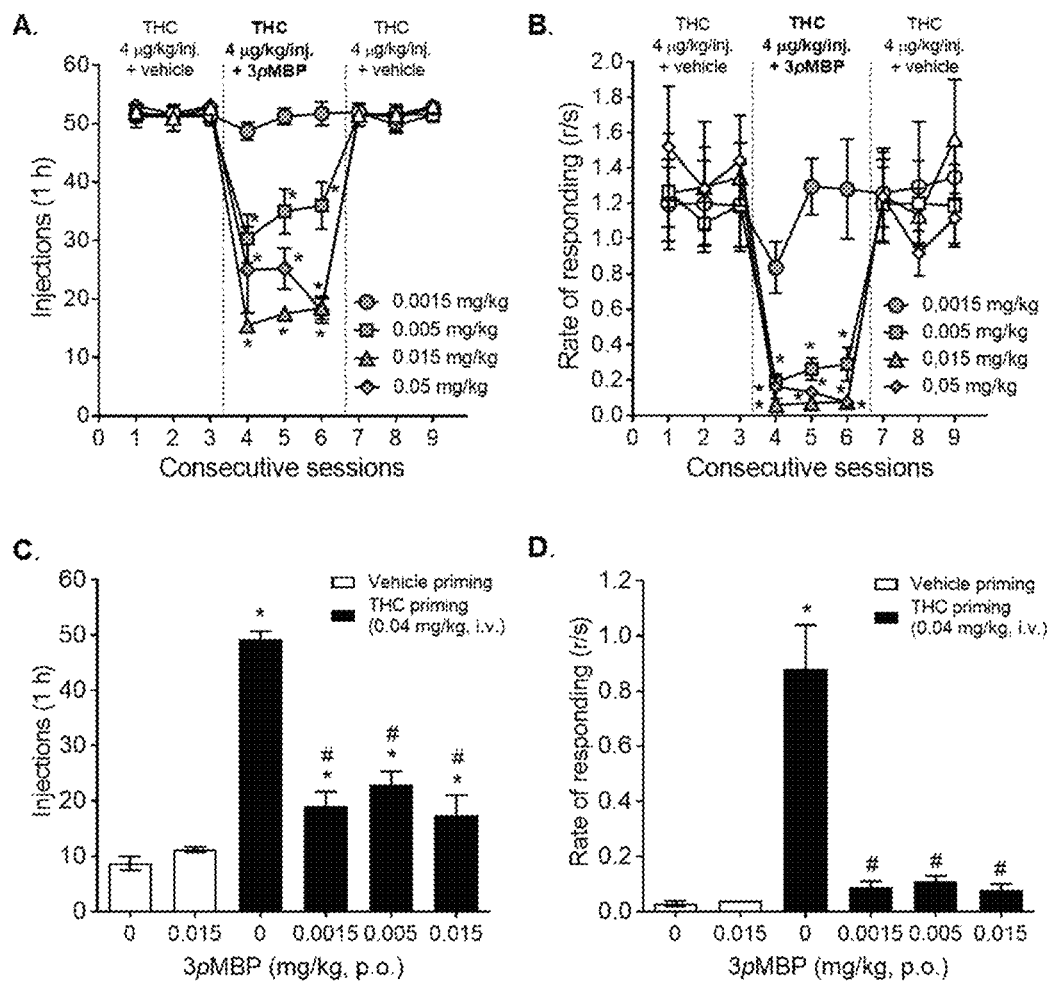

FIG. 7 Effects of 3pMBP on THC self-administration and reinstatement in monkeys

FIG. 7A: 3pMBP dose dependently decreases the number of injections of THC in squirrel monkeys during intravenous self-administration (1-h sessions) of THC (4 µg/kg/injection) under a fixed-ratio ten (FR10)

*$p<0.05$, vs. vehicle of 3pMBP+THC (Bonferroni test).

FIG. 7B: 3pMBP dose dependently decreases the response rates for THC in squirrel monkeys during intravenous self-administration (1-h sessions) of THC (4 µg/kg/injection) under a fixed-ratio ten (FR10).

*$p<0.05$, vs. vehicle of 3pMBP+THC (Bonferroni test).

FIG. 7C: 3pMBP (per os) reduces THC-induced reinstatement (0.04 mg/kg) of drug seeking in monkeys. Bar represents mean±SEM (n=4) of number of vehicle injections. "0 mg/kg" represents vehicle of 3pMBP.

*$p<0.05$, vs. 'vehicle priming' (Tukey test).
$p<0.05$, vs. 'THC priming', (Tukey test).

FIG. 7D: 3pMBP (per os) reduces the rate of responses during the test for THC-induced reinstatement (0.04 mg/kg) of drug seeking in monkeys. Bar represents mean±SEM (n=4) of the rates of responding. "0 mg/kg" represents vehicle of 3pMBP.

*$p<0.05$, vs. 'vehicle priming' (Tukey test).
$p<0.05$, vs. 'THC priming', (Tukey test).

Figure 8:
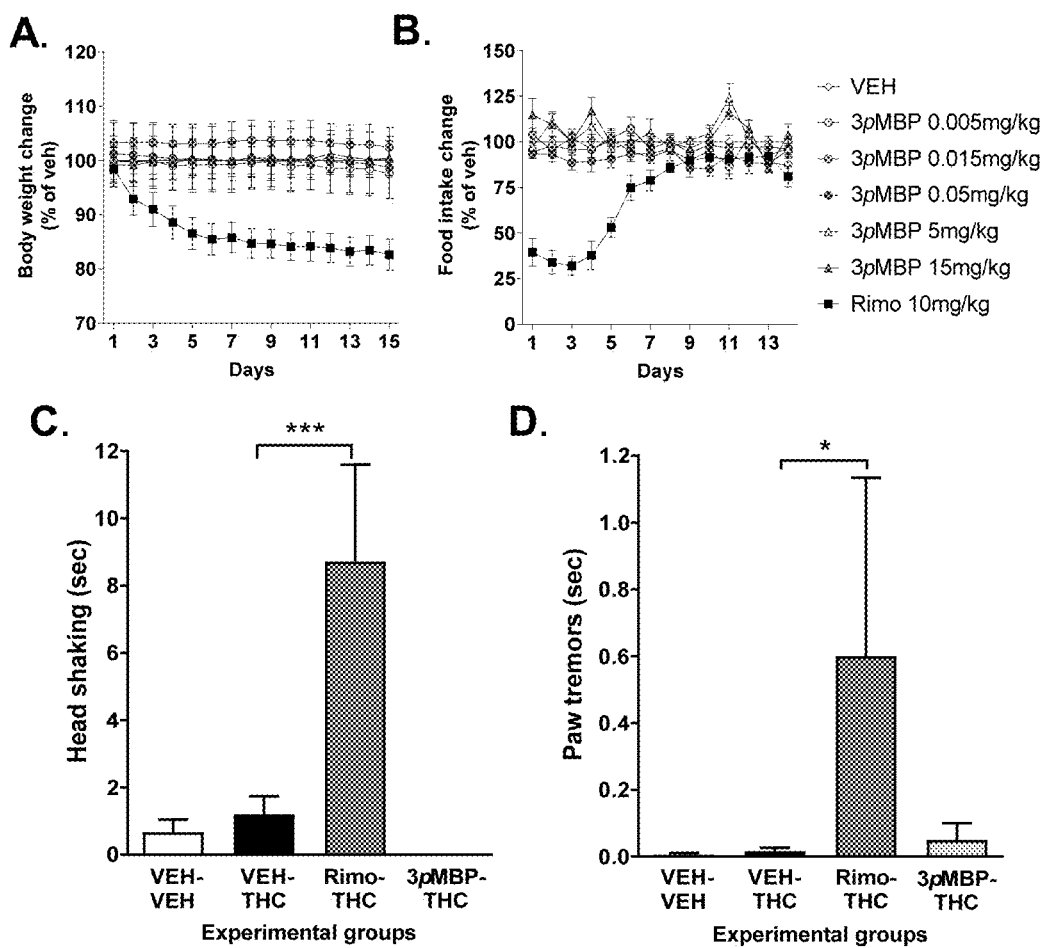

FIG. 8 Effects of 3pMBP and rimonabant on food intake and body weight and on THC-induced withdrawal.

FIG. 8A: Effects of 3pMBP and rimonabant on body weight in obese mice.

As compared to vehicle-treated animals (VEH), Rimonabant (Rimo 10 mg/kg; ip), but not 3pMBP (0.005, 0.015, 0.05, 5 and 15 mg/kg; per os), decreases body weight in obese mice.

Days 1 to 4: no significant effect of rimonabant.
Days 5 to 7: $p<0.05$, Rimo vs VEH (Dunnett test).
Days 7 to 15: $p<0.01$, Rimo vs VEH (Dunnett test).

FIG. 8B: Effects of 3pMBP and rimonabant on food intake in obese mice.

As compared to vehicle-treated animals (VEH), Rimonabant (Rimo 10 mg/kg; ip), but not 3pMBP (0.005, 0.015, 0.05, 5 and 15 mg/kg; per os), decreases food intake in obese mice. Day 1 to 5: $p<0.001$, Rimo vs VEH (Tukey test).

FIG. 8C: Effects of 3pMBP and rimonabant on duration of head shaking.

Rimonabant (Rimo, 10 mg/kg; ip), but not 3pMBP (0.15 mg/kg; per os) increases the duration of head shaking in mice that received a repeated treatment with THC (20 mg/kg; ip) administrations in comparison with animals repeatedly treated with THC receiving an injection of vehicle (VEH).

***$p<0.001$; VEH-THC vs Rimo-THC group (Student t-test).

FIG. 8D: Effects of 3pMBP and rimonabant on duration of paw tremors.

Rimonabant (Rimo, 10 mg/kg; ip), but not 3pMBP (0.15 mg/kg; per os) increases the duration of paw tremors in mice that received a repeated treatment with THC (20 mg/kg; ip) administrations in comparison with animals repeatedly treated with THC receiving an injection of vehicle (VEH).

*$p<0.05$; VEH-THC vs Rimo-THC group (Student t-test).

Figure 9:
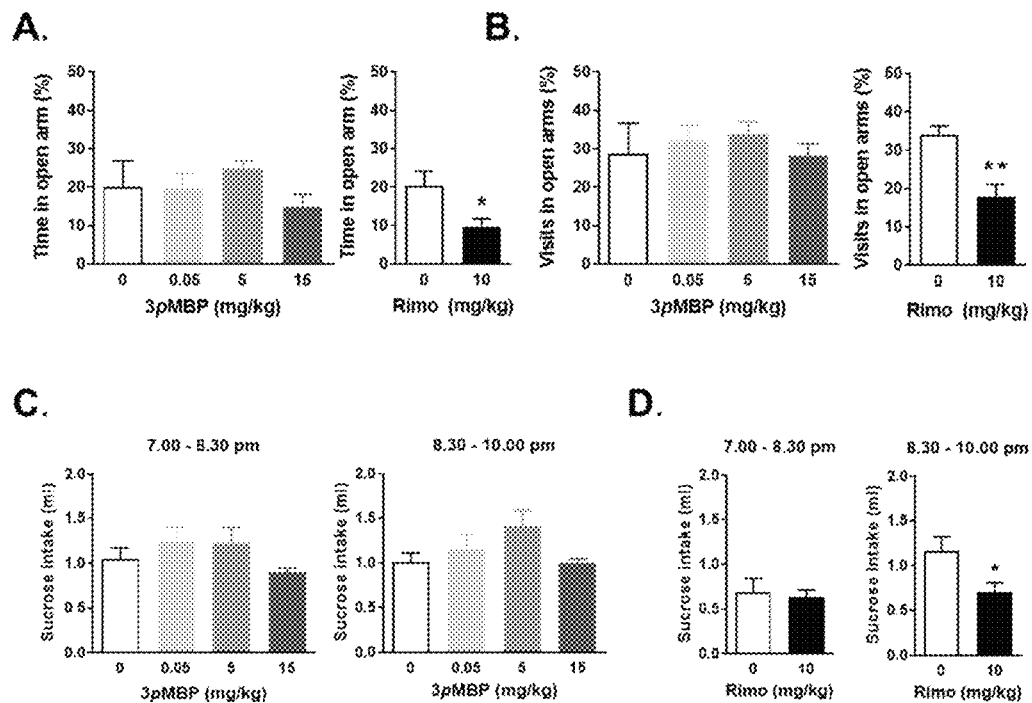

FIG. 9: Effects of the repeated administrations of 3pMBP or rimonabant on anxiety and depression-related behaviors in mice.

FIG. 9A: Effects in mice of repeated (28 days, once a day) administrations of 3pMBP (0, 0.05, 5, 15 mg/kg, per os) or of rimonabant (Rimo 0 and 10 mg/kg; ip) on anxiety-related behaviors as measured by the percentage of time spent in the open arms of the elevated plus maze. 3pMBP has no effect on the time spent in open arms whereas rimonabant decreases the time spent in open arms.

FIG. 9B: Effects in mice of repeated (28 days, once a day) administrations of 3pMBP (0, 0.05; 5; 15 mg/kg, per os) or of rimonabant (Rimo 0 and 10 mg/kg; ip) on anxiety-related behaviors as measured by the percentage of visits in the open arms of the elevated plus maze. 3pMBP has no effect on the visits in open arms whereas rimonabant decreases the percentage of visits in open arms.

**$p<0.01$; *$p<0.05$; Rimo vs vehicle (0 mg/kg) (Student t-test).

FIG. 9C: Effects in mice of repeated (28 days, once a day) administrations of 3pMBP (0, 0.05; 5; 15 mg/kg, per os) on depression-related behaviors as measured in the sucrose preference test. 3pMBP has no effect on sucrose intake.

FIG. 9D: Effects in mice of repeated (28 days, once a day) administrations of rimonabant (Rimo 0 and 10 mg/kg; ip) on depression-related behaviors as measured in the sucrose preference test. Rimonabant decreases sucrose intake (8.30-10 pm delay).

*$p<0.05$, Rimo vs vehicle (0 mg/kg) (Student t-test).

Figure 10:
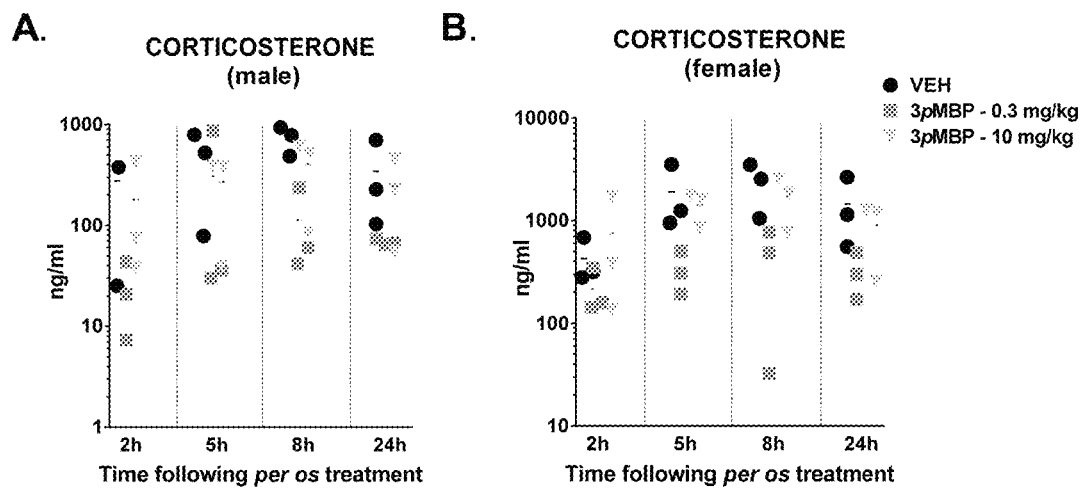

FIG. 10: Effect of 3pMBP on plasma concentrations of corticosterone in mice.

FIG. 10A: In male mice, the administration of 3pMBP (0.3 or 10 mg/kg; per os) or vehicle (VEH) has no significant effect on plasma concentrations of corticosterone measured 2, 5, 8 and 24 hours following administration.

FIG. 10B: In female mice, the administration of 3pMBP (0.3 or 10 mg/kg; per os) or vehicle (VEH) has no significant effect on plasma concentrations of corticosterone measured 2, 5, 8 and 24 hours following administration.

Data are represented in log(10) scale.

Figure 11:
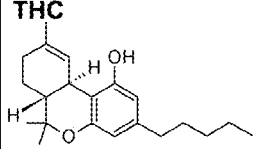
Figure 11:
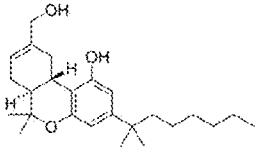
Figure 11:
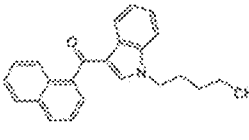
Figure 11:
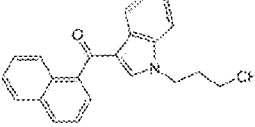
Figure 11:
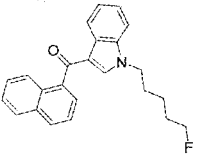
Figure 11:
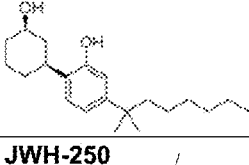
Figure 11:
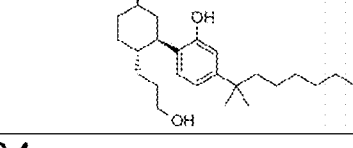
Figure 11:
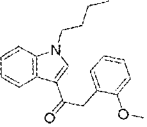
Figure 11:
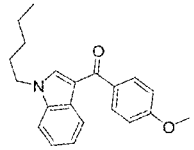
Figure 11:
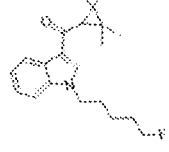
Figure 11:
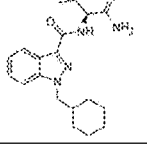
Figure 11:
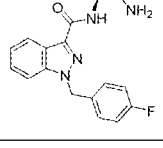
Figure 11:
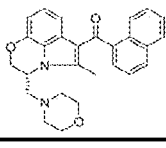

FIG. 11: A table providing examples of synthetic cannabinoids.

FIG. 12: A table providing a comparison of the toxic effect of 3pMBP and rimonabant in GLP studies, where ND=Not Determined, and safety index is calculated from 10 mg/kg for Rimonabant and 0.005 for 3pMBP.

DETAILED DESCRIPTION

The present invention generally relates to a compound of Formula (I):

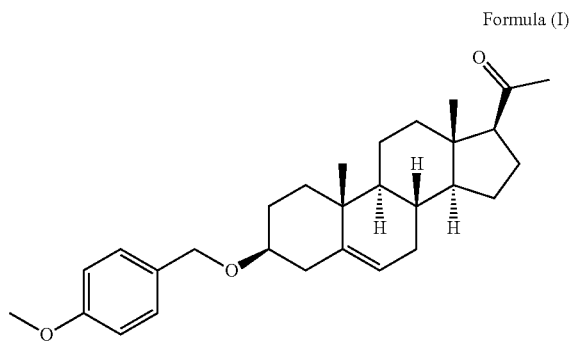

Formula (I)

for use in the treatment of a Cannabinoids-Related Disorder.

The compound of the present invention, 3β-(4-methoxybenzyloxy)pregn-5-en-20-one does not block the entire activity of the target receptor but only part of its activity. The specific target receptor of the compound of the present invention is the CB1 receptor.

The compound of Formula (I) is able to reproduce the effects of a newly discovered brain mechanism that provides an endogenous negative feedback, regulating an over activation of the CB1. It is important to note that this regulatory mechanism is triggered only when CB1 is strongly over activated, but not when the activation of the receptor is within a more physiological range. This is why the compound of the present invention is extremely potent in blocking the effects of CB1 agonist THC and is thus effective for the treatment of Cannabinoids-Related Disorders. Furthermore, because of its signaling specific action mechanism the compound of the present invention has no effects on behavior per se in healthy subjects in which the CB1 is not activated by cannabinoids.

The mechanism of action of the compound of the present invention is in this respect very different from the one of CB1 orthosteric antagonists, which by blocking the binding of endogenous and exogenous agonists of the CB1 receptor, induce a complete inhibition of all CB1 activity and disrupt behavior per se. In addition, the mechanism of action of antagonists does not exist physiologically, i.e. to the best of our knowledge, there are no endogenous compounds, which like antagonists, block the binding of a CB1 agonists to the receptor. Because of the artificial nature of this mechanism of action, these antagonists, in addition to correct for an over-activation of a target receptor, generally lower its activity below basal levels, disrupting physiology and generating side effects.

The different mechanism of action between the compound of the present invention and orthosteric antagonists, such as rimonabant, explains why both drugs can inhibit THC effects but do not share other behavioral effects.

Hence, the compound of the present invention is not a CB1 antagonist and as such does not block all the cellular effects of THC, as the orthosteric CB1 antagonist rimonabant does. Actually, the compound of the present invention transforms THC into a cAMP-biased agonist of the CB1.

A biased agonist is a compound that is able to activate only some of the cellular effects mediated by its target receptor. In the case of CB1, the two major effects of an agonist, such as THC, are to simultaneously inhibit the production of cAMP and stimulate the activity of the MAPK. A biased agonist of the CB1 would then be able to either selectively inhibit cAMP (cAMP-biased CB1 agonist) or activate the MAPK (MAPK biased CB1 agonist). When the compound of the present invention is on board, THC is still able to inhibit the production of cAMP but not to activate MAPK.

In other words, the compound of the present invention has transformed THC into a cAMP-biased agonist.

The preclinical data obtained with the compound of the present invention indicate that as a cAMP-biased agonist, THC loses most of its unconditioned and conditioned behavioral effects, which becomes less reinforcing and less able to reinstate drug seeking after a period of drug discontinuation.

However, THC is still having some of its cellular effects. This is probably why the compound of the present invention does not precipitate withdrawal in THC-dependent mice, whilst rimonabant does.

Advantageously, the compound of the present invention does not display the behavioral effects of CB1 antagonists. Indeed, CB1 orthosteric antagonists block the entire cellular activity of a receptor, whilst the compound of the present invention blocks only some of them.

Still advantageously and more generally no adverse effects have been observed with the compound of the present invention.

The lack of adverse effects, and in many cases, no effect of the compound of the present invention in rodents and dogs are probably due to the specific structure, the mechanism of action and Adsorption/Distribution/Metabolism/Excretion characteristics of the compound of the present invention.

The inventors demonstrate that the compound of the invention has concomitant characteristics that make it a unique ideal tool to treat Cannabinoids-Related Disorders.

These characteristics include but are not limited to:

1. The compound of the present invention has a unique mechanism of action tailored as an endogenous brain mechanism to overcome an over activation of the CB1 receptor, but seems to have no effect on the basal activity of the receptor. Disruption of the basal activity of the target system is often responsible for some of the adverse effects of antagonists. In addition, the compound of the present invention is very selective and does not interact with any of the 85 receptors tested. Off-target effects are often responsible for some of the adverse effects of new chemical entities. Cellular activity of the CB1 receptor is then inhibited in a selective and signaling-specific manner.
2. The compound of the present invention shows in vivo a very high potency in inhibiting a large spectrum of unconditioned and conditioned effects of CB1 agonists including, but not limited to THC.
3. The compound of the present invention has none of the adverse effects of orthosteric CB1 antagonists, including but not limited to: a. decrease in food intake; b. increase in anxiety- and depression-related behaviors: c. increased glucocorticoid secretion; d. precipitated withdrawal in THC dependent animals; e. induction of clonic convulsion and clinical sign related to an impairment of the central nervous system; f. hepatotoxicity.
4. The compound of the present invention causes no relevant changes in behavior per se, even at doses that are thousands of times higher than the $ID_{50}$ for the inhibition of THC.

5. The compound of the present invention has good Absorption, Distribution, Metabolism and Excretion characteristics with not significant conversion in major metabolites including but not limited to downstream active steroids.
6. The compound of the present invention presents a good access to the brain.
7. The compound of the present invention does not modify the activity of the major endogenous metabolic enzyme and transport systems.
8. The compound of the present invention has no adverse and toxic effects, in vitro and in vivo, at doses thousands of time higher than the $ID_{50}$ for the inhibition of THC effects. Consequently, the compound of the present invention has a very good therapeutic index >7200.

According to the present invention, "Cannabinoids-Related Disorders" or "Cannabinoids-Related Disorder" or "CRDs" include Cannabinoids Use Disorder (CUD); Cannabinoids Intoxication; Cannabinoids Withdrawal; Other Cannabinoids-Induced Disorders; Unspecified Cannabinoids-Related Disorder; Cannabinoids Hyperemesis Syndrome, Cannabinoids-Induced Catatonia and all the disorders that can be attributed to the use of cannabinoids.

In order to exemplify the principal Cannabinoids-Related Disorders (CRD) we use here the criteria of the fifth edition of the Diagnostic and Statistical Manual of Mental Disorders (DSM-5™) that refers to *cannabis* and synthetic cannabinoids.

However, this is not an exclusive description of Cannabinoids-Related Disorders but encompass similar disorders described in other diagnostic manuals including but not limited to the International Classification of Diseases (World Health Organization) and more generally all the disorders induced by preparation derived from *cannabis* or containing synthetic cannabinoids.

Examples of such disorders are well described in the publication of 2016 of the World Health Organization entitled "The health and social effects of nonmedical *cannabis* use". Short-term effects of cannabinoids use include disorders such as impairment of cognition and coordination, anxiety and psychotic symptoms, acute toxicity, acute cardiovascular effects and acute effects on lungs and airways. Long-term cannabinoids use implies not only adverse psychosocial and mental health outcomes but also Cannabinoids-related cardiovascular disorders and Cannabinoids-related ischaemic stroke.

"Cannabinoids Use Disorder" or "CUD" should be understood as a problematic pattern of cannabinoids use leading to clinically significant impairment or distress, as manifested by at least two of the following, occurring within a 12-month period:
1. Cannabinoids are often taken in larger amounts or over a longer period than was intended.
2. There is a persistent desire or unsuccessful efforts to cut down or control cannabinoids use.
3. A great deal of time is spent in activities necessary to obtain cannabinoids, use cannabinoids, or recover from its effects.
4. Craving, or a strong desire or urge to use cannabinoids.
5. Recurrent cannabinoids use resulting in a failure to fulfill major role obligations at work, school, or home.
6. Continued cannabinoids use despite having persistent or recurrent social or interpersonal problems caused or exacerbated by the effects of cannabinoids.
7. Important social, occupational, or recreational activities are given up or reduced because of cannabinoids use.
8. Recurrent cannabinoids use in situations in which it is physically hazardous.
9. Cannabinoids use is continued despite knowledge of having a persistent or recurrent physical or psychological problem that is likely to have been caused or exacerbated by cannabinoids.
10. Tolerance, as defined by either of the following:
    a. A need for markedly increased amounts of cannabinoids to achieve intoxication or desired effect.
    b. Markedly diminished effect with continued use of the same amount of cannabinoids.
11. Withdrawal, as manifested by either of the following:
    a. The characteristic withdrawal syndrome for cannabinoids.
    b. Cannabinoids (or a closely related substance) is taken to relieve or avoid withdrawal symptoms.

According to the DSM-5™, Cannabinoids Use Disorder, will be considered as "mild" if 2 to 3 symptoms are presents, as "moderate" if 4 to 5 symptoms are presents and "severe" if 6 or more symptoms are presents.

As used herein, "Cannabinoids Intoxication" should be diagnosing with the following criteria:
A. Recent use of *cannabis* or of a synthetic cannabinoid.
B. Clinically significant problematic behavioral or psychological changes (e.g., impaired motor coordination, euphoria, anxiety, sensation of slowed time, impaired judgment, social withdrawal) that developed during, or shortly after, cannabinoids use.
C. Two (or more) of the following signs or symptoms developing within 2 hours of cannabinoids use:
   1. Conjunctival injection.
   2. Increased appetite.
   3. Dry mouth.
   4. Tachycardia.
D. The signs or symptoms are not attributable to another medical condition and are not better explained by another mental disorder, including intoxication with another substance.

The term "Cannabinoids Withdrawal" disorder should be diagnosing with the following criteria:
A. Cessation of cannabinoids use that has been heavy and prolonged (i.e., usually daily or almost daily use over a period of at least a few months).
B. Three (or more) of the following signs and symptoms develop within approximately 1 week after Criterion A:
   1. Irritability, anger, or aggression.
   2. Nervousness or anxiety.
   3. Sleep difficulty (e.g., insomnia, disturbing dreams).
   4. Decreased appetite or weight loss.
   5. Restlessness.
   6. Depressed mood.
   7. At least one of the following physical symptoms causing significant discomfort: abdominal pain, shakiness/tremors, sweating, fever, chills, or headache.
C. The signs or symptoms in Criterion B cause clinically significant distress or impairment in social, occupational, or other important areas of functioning.
D. The signs or symptoms are not attributable to another medical condition and are not better explained by another mental disorder, including intoxication or withdrawal from another substance.

According to the DSM-5™ the "Other Cannabinoids-Induced Disorders" are cannabinoids-induced anxiety disorder; cannabinoids-induced psychotic disorder; cannabinoids-induced sleep disorder; cannabinoids intoxication delirium. These cannabinoids-induced disorders are diagnosed instead of cannabinoids intoxication or cannabinoids withdrawal when the symptoms are sufficiently severe to warrant independent clinical attention.

The "cannabinoids-induced psychotic disorder" should be diagnosing with the following criteria:
A. Presence of one or both of the following symptoms:
   1. Delusions.
   2. Hallucinations.
B. There is evidence from the history, physical examination, or laboratory findings of both (1) and (2):
   1. The symptoms in Criterion A developed during or soon after cannabinoids intoxication or withdrawal or after exposure to a medication.
   2. The involved cannabinoids is capable of producing the symptoms in Criterion A.
C. The disturbance is not better explained by a psychotic disorder that is not substance-induced. Such evidence of an independent psychotic disorder could include the following:
   The symptoms preceded the onset of the cannabinoids use; the symptoms persist for a substantial period of time (e.g., about 1 month) after the cessation of acute withdrawal or severe intoxication: or there is other evidence of an independent non-substance/medication-induced psychotic disorder (e.g., a history of recurrent non substance/medication-related episodes).
D. The disturbance does not occur exclusively during the course of a delirium.
E. The disturbance causes clinically significant distress or impairment in social, occupational, or other important areas of functioning.

This diagnosis should be made instead of a diagnosis of substance intoxication or substance withdrawal only when the symptoms in Criterion A predominate in the clinical picture and when they are sufficiently severe to warrant clinical attention.

The "cannabinoids-induced anxiety disorder" should be diagnosing with the following criteria:
A. Panic attacks or anxiety is predominant in the clinical picture.
B. There is evidence from the history, physical examination, or laboratory findings of both (1) and (2):
   1. The symptoms in Criterion A developed during or soon after cannabinoids intoxication or withdrawal or after exposure to cannabinoids.
   2. The involved cannabinoids are capable of producing the symptoms in Criterion A.
C. The disturbance is not better explained by an anxiety disorder that is not cannabinoids-induced. Such evidence of an independent anxiety disorder could include the following: The symptoms precede the onset of the substance/medication use; the symptoms persist for a substantial period of time (e.g., about 1 month) after the cessation of acute withdrawal or severe intoxication: or there is other evidence suggesting the existence of an independent non-substance/medication-induced anxiety disorder (e.g., a history of recurrent non-substance/medication-related episodes).
D. The disturbance does not occur exclusively during the course of a delirium.
E. The disturbance causes clinically significant distress or impairment in social, occupational, or other important areas of functioning.
Note: This diagnosis should be made instead of a diagnosis of cannabinoids intoxication or cannabinoids withdrawal only when the symptoms in Criterion A predominate in the clinical picture and they are sufficiently severe to warrant clinical attention.

The "Cannabinoids-induced sleep disorder" should be diagnosing with the following criteria:
A. A prominent and severe disturbance in sleep.
B. There is evidence from the history, physical examination, or laboratory findings of both (1) and (2):
   1. The symptoms in Criterion A developed during or soon after cannabinoids intoxication or after withdrawal from or exposure to cannabinoids.
   2. The involved cannabinoids are capable of producing the symptoms in Criterion A.
C. The disturbance is not better explained by a sleep disorder that is not cannabinoids-induced. Such evidence of an independent sleep disorder could include the following: The symptoms precede the onset of the cannabinoids use; the symptoms persist for a substantial period of time (e.g., about 1 month) after the cessation of acute withdrawal or severe intoxication; or there is other evidence suggesting the existence of an independent non-cannabinoids-induced sleep disorder (e.g., a history of recurrent non-substance/medication-related episodes).
D. The disturbance does not occur exclusively during the course of a delirium.
E. The disturbance causes clinically significant distress or impairment in social, occupational, or other important areas of functioning.
Note: This diagnosis should be made instead of a diagnosis of cannabinoids intoxication or cannabinoids withdrawal only when the symptoms in Criterion A predominate in the clinical picture and when they are sufficiently severe to warrant clinical attention.

The "Intoxication Delirium" should be diagnosing with the following criteria:
A. A disturbance in attention (i.e., reduced ability to direct, focus, sustain, and shift attention) and awareness (reduced orientation to the environment).
B. The disturbance develops over a short period of time (usually hours to a few days), represents a change from baseline attention and awareness, and tends to fluctuate in severity during the course of a day.
C. An additional disturbance in cognition (e.g., memory deficit, disorientation, language, visuospatial ability, or perception).
D. The disturbances in Criteria A and C are not better explained by another preexisting, established, or evolving neurocognitive disorder and do not occur in the context of a severely reduced level of arousal, such as coma.
E. There is evidence from the history, physical examination, or laboratory findings that the disturbance is a direct physiological consequence of cannabinoids intoxication or withdrawal.

A diagnosis of Cannabinoids Intoxication Delirium should be made instead of cannabinoids intoxication when the symptoms in Criteria A and C predominate in the clinical picture and when they are sufficiently severe to warrant clinical attention.

A diagnosis of cannabinoids withdrawal delirium should be made instead of substance withdrawal when the symptoms in Criteria A and C predominate in the clinical picture and when they are sufficiently severe to warrant clinical attention.

As used herein, and according to the DSM-5™ the category of "Unspecified Cannabinoid-Related Disorder" applies to presentations in which symptoms characteristic of a Cannabinoid-Related Disorder that cause clinically significant distress or impairment in social, occupational, or other important areas of functioning predominate but do not meet the full criteria for any specific Cannabinoids-Related Disorders or any of the disorders in the substance-related and addictive disorders diagnostic class.

As used herein "Cannabinoids Hyperemesis Syndrome" applies to presentations characterized by cannabinoids use, cyclic episodes of nausea and vomiting often associated with frequent hot bathing. The clinical course of Cannabinoids Hyperemesis Syndrome may be divided into three phases: prodromal, hyperemetic, and recovery phase. The hyperemetic phase usually ceases within 48 hours. Patients often demonstrate the learned behavior of frequent hot bathing, which produces temporary cessation of nausea, vomiting, and abdominal pain (Galli et al., 2011).

As used herein "Cannabinoids-Induced Catatonia" applies to presentations characterized by cannabinoids use followed by a catatonic-like state, with reduced mobility, alertness and responsivity to external stimulation as the prevalent clinical symptomatology (Adams et al 2017, Khan et al., 2016).

Hence, the present invention relates to a compound of Formula (I):

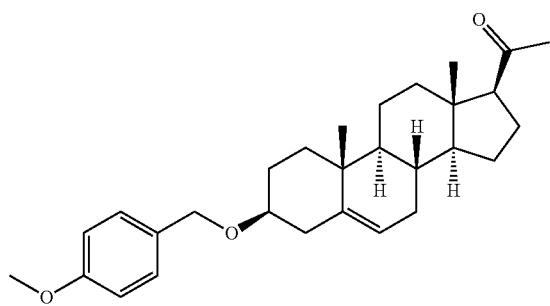

Formula (I)

for use in the treatment of a Cannabinoids-Related Disorder selected among Cannabinoids Use Disorder (CUD); Cannabinoids Intoxication; Cannabinoids Withdrawal; Other Cannabinoids-Induced Disorders, Unspecified Cannabinoids-Related Disorder; Cannabinoids Hyperemesis Syndrome and Cannabinoids-Induced Catatonia.

As used herein, "cannabinoids" refer to substances that are full or partial agonists acting on cannabinoid receptors. Cannabinoids include natural extracts and synthetic compounds also known as *cannabis*-like substances.

Two main types of cannabinoid (CB) receptors have been described: CB1 and CB2 receptors.

Typically, natural cannabinoids could be extracted from the *Cannabis* L. plant in particular *Cannabis sativa*.

Over time, the plant material obtained from *Cannabis* L. plant has accumulated many names (e.g., weed, pot, herb, grass, reefer, maryjane, dagga, dope, bhang, skunk, boom, gangster, kif, and ganja). Cannabinoids users can either intake parts of the plant, for example the flower or the leaves, or different type of concentrated extraction of the plant of which one of the most commonly used is hashish. Plants components or plant extracts are usually smoked or ingested with several food preparations.

*Cannabis* is a psychoactive plant that contains more than 500 components, of which 104 cannabinoids have presently been identified.

Δ9-tetrahydrocannabinol (THC) is the major psychoactive component in *cannabis* plant. *Cannabis* potency is primarily evaluated according to the THC concentration. For this reason, an extract containing pure THC (pure gold) can be purchased and are used by cannabinoids consumers. The adverse effects after acute or regular *cannabis* use are in direct relation to THC concentrations in the product (Lafaye et al., 2017).

Cannabidiol (CBD), cannabinol (CBN), cannabavarin (THCV), cannabigerol (CBG), cannabichromene (CBC), delta-8-THC, cannabicyclol (CBL), cannabitriol (CBT), and cannabielsoin are among the many different naturally-occurring cannabinoids containing in *cannabis* plant. Most are known to have psychoactive properties.

Synthetic cannabinoids bind with cannabinoid receptors and elicit effects similar to Δ9-tetrahydrocannabinol (THC). Some examples of synthetic cannabinoids are described but without limitation in FIG. 11.

Substances containing Synthetic cannabinoids (SCBs) are also known under the brand names of "Spice," "K2," "herbal incense," "Cloud 9," "Mojo".

Hence, and as used herein, Cannabinoids-Related Disorders include disorders that are associated with the use of cannabinoids.

The terms "3β-(4-methoxybenzyloxy)pregn-5-en-20-one" or "$C_{29}H_{40}O_3$," or "3β-(para-methoxybenzyloxy) pregn-5-en-20-one" or "3pMBP" or "1-((3S,8S,9S,10R,13S, 14S,17S)-3-((4-methoxybenzyl)oxy)-10,13-dimethyl-2,3,4, 7,8,9,10,11,12,13,14,15,16,17-tetradecahydro-1H-cyclopenta[a]phenanthren-17-yl)ethan-1-one" designate the pregnenolone derivative according to the present invention which has the following formula (I):

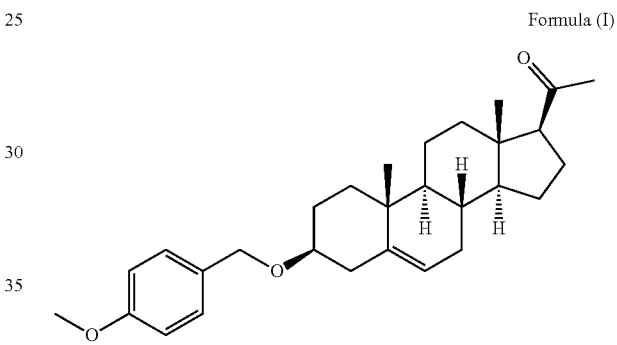

Formula (I)

The term "treatment" or "method of treating" or its equivalent is not intended as an absolute term and, when applied to, for example, Cannabinoids-Related Disorders refers to a procedure or course of action that is designed to reduce or eliminate or to alleviate one or more symptoms of Cannabinoids-Related Disorders.

Often, a "treatment" or a "method of treating" Cannabinoid-Related Disorders will be performed even with a low likelihood of success but is nevertheless deemed to induce an overall beneficial effect. Treatment of Cannabinoids-Related Disorders refers, for example, to delay of onset, reduced frequency of one or more symptoms, or reduced severity of one or more symptoms associated with the disorder. In some circumstances, the frequency and severity of one or more symptoms is reduced to non-pathological levels.

More particularly, the term of "treatment" or a "method of treating" of Cannabinoids-Related Disorders refers to an improvement of clinical behavioral or biological criteria in the subject. For instance, "treatment" or a "method of treating" of Cannabinoids Use Disorders may refer in particular to a decrease in the number and/or intensity of criteria 1 to 11 as defined above for the Cannabinoids Use Disorders. It can also refer to prevention or delay of the onset or reduction of the intensity of clinical behavioral or biological criteria associated to other Cannabinoids-Related Disorders.

The present invention also relates to a process for the manufacture of the compound of Formula (I), which comprises three chemical stages from readily available starting material pregnenolone.

Hence, the present invention relates to a process for the manufacture of the compound of Formula (I) which comprises:

A first stage of protecting pregnenolone:

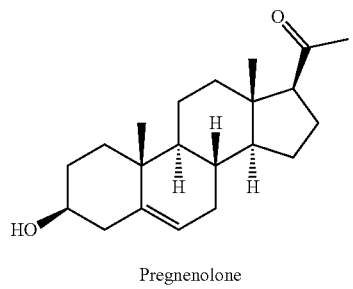

Pregnenolone into a compound of Formula (IV):

Formula (IV)

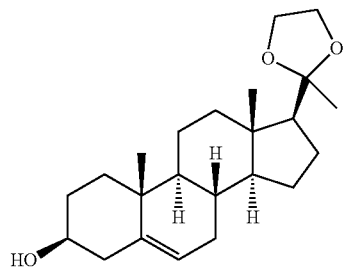

A second step wherein said compound of Formula (IV) reacts with a compound of Formula (III):

Formula (III)

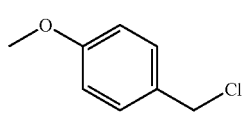

in order to obtain a compound of Formula (II):

Formula (II)

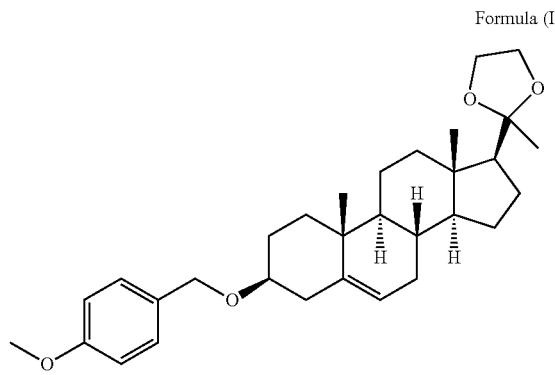

A third step wherein compound of Formula (II) is deprotected in order to obtain the compound of Formula (I):

Formula (I)

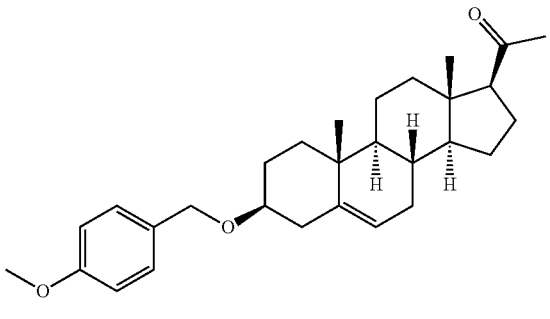

Figure 1:
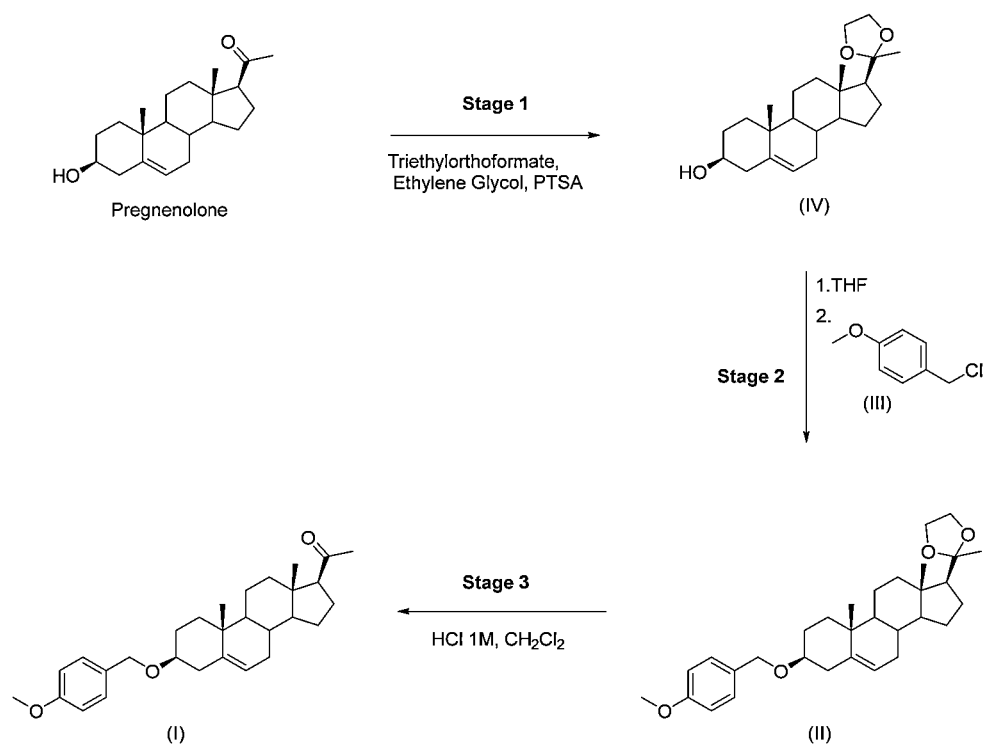
FIG. 1: Compound of formula (I) (3pMBP) synthesis flowchart

The process for the manufacture of the compound of Formula (I) is described in FIG. 1.

The present invention also concerns a pharmaceutical composition comprising a compound of Formula (I):

Formula (I)

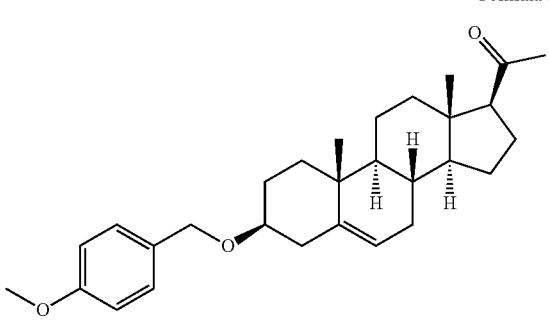

and at least one pharmaceutically acceptable excipient.

The form of the pharmaceutical composition, the route of administration, the dosage and the regimen naturally depend upon the condition to be treated, the severity of the illness, the age, weight, and sex of the patient, etc.

While it is possible for the compound of the present invention to be administered alone, it is preferable to formulate it into a pharmaceutical composition in accordance with standard pharmaceutical practice. Thus, the invention also provides a pharmaceutical composition comprising a compound of formula (I) in admixture with at least one pharmaceutically acceptable excipient.

There is further provided by the present invention a process of preparing a pharmaceutical composition, which process comprises mixing a compound of Formula (I), together with at least one pharmaceutically acceptable excipient.

The pharmaceutical composition will typically comprise at least one pharmaceutically acceptable excipient. Acceptable excipients for therapeutic use are well known in the pharmaceutical art, and are described, for example, in Remington's Pharmaceutical Sciences, $21^{st}$ Edition 2011. The choice of pharmaceutical excipient can be selected with regard to the intended route of administration and standard pharmaceutical practice. The excipient must be acceptable in the sense of being not deleterious to the recipient thereof. The at least one pharmaceutically acceptable excipient may be for example, a binder, a diluent, a carrier, a lubricant, a disintegrator, a wetting agent, a dispersing agent, a suspending agent, and the like.

The routes for administration (delivery) of the above defined compound include, but are not limited to: oral (e.g. as a tablet, capsule, or as an ingestible solution), topical, mucosal (e.g. as a nasal spray or aerosol for inhalation), nasal, gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural, sublingual.

Preferred administration routes include oral, mucosal, parenteral, and sublingual.

For example, the compound can be administered orally in the form of tablets, coated tablets, pills, capsules, soft gelatin capsules, oral powders, granules, ovules, elixirs, solutions or suspensions, which may contain flavouring or colouring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, a disintegrant such as starch (preferably corn, potato or tapioca starch), sodium starch glycollate, croscarmellose sodium and certain complex silicates, a binder such as polyvinylpyrrolidone, hydroxypropylmethylcellulose (HPMC), hydroxypropylcellulose (HPC), sucrose, gelatin and acacia, a lubricant such as magnesium stearate, stearic acid, glyceryl behenate. Solid compositions of a similar type may also be employed as fillers in hard gelatin capsules. Preferred excipients in this regard include lactose, saccharose, sorbitol, mannitol, potato starch, corn starch, amylopectin, cellulose derivatives or gelatin. Hard gelatin capsules may contain granules of the compound of the invention.

Soft gelatin capsules may be prepared with capsules containing the compound of the invention, vegetable oil, waxes, fat, or other suitable vehicle for soft gelatin capsules. As an example, the acceptable vehicle can be an oleaginous vehicle, such as a long chain triglyceride vegetable oil (e.g. corn oil).

Dispersible powders and granules suitable for preparation of an aqueous suspension by the addition of water may contain the active ingredient in a mixture with dispersing agents, wetting agents, and suspending agents and one or more preservatives. Additional excipients, for example sweetening, flavoring and coloring agents, may also be present. These compositions may be preserved by the addition of an anti-oxidant such as ascorbic acid. Liquid dosage forms for oral administration may include pharmaceutically acceptable, solutions, emulsions, suspensions, syrups, and elixirs containing inert diluents commonly used in the art, such as water or an oleaginous vehicle. Liquid dosage form may be presented as a dry product for constitution with water or other suitable vehicle before use. Such compositions may also comprise adjuvants, such as wetting agents, emulsifying and suspending agents, complexing agents such as 2-hydroxypropyl-beta-cyclodextrin, sulfobutylether-beta-cylodextrin, and sweetening, flavouring, perfuming agents, colouring matter or dyes with diluents such as water, ethanol, propylene glycol and glycerin, and combinations thereof. These compositions may be preserved by the addition of an anti-oxidant such as butylated hydroxyanisol or alpha-tocopherol.

Finely divided powder of the compound of the invention may be prepared for example by micronisation or by processes known in the art. The compound of the invention may be milled using known milling procedures such as wet milling to obtain a particle size appropriate for tablet formation and for other formulation types.

If the compound of the present invention is administered parenterally, then examples of such administration include one or more of: intravenously, intraarterially, intraperitoneally, intrathecally, intraventricularly, intraurethrally, intrasternally, intracranially, intramuscularly or subcutaneously administering the agent; and/or by using infusion techniques.

The compound of the invention can be administered via the parenteral route with a ready available or a depot-type formulation.

The pharmaceutical compositions for the parenteral administration of a ready available formulation may be in the form of a sterile injectable aqueous or oleagenous solution or suspension in a non-toxic parenterally-acceptable diluent or solvent and may contain formulatory agents such as suspending, stabilising dispersing, wetting and/or complexing agents such as cyclodextrin e.g. 2-hydroxypropyl-beta-cyclodextrin, sulfobutylether-beta-cylodextrin.

The depot-type formulation for the parenteral administration may be prepared by conventional techniques with pharmaceutically acceptable excipient including without being limited to, biocompatible and biodegradable polymers (e.g. poly($\beta$-caprolactone), poly(ethylene oxide), poly(glycolic acid), poly[(lactic acid)-co-(glycolic acid) . . . )], poly(lactic acid) . . . ), non-biodegradable polymers (e.g. ethylene vinylacetate copolymer, polyurethane, polyester (amide), polyvinyl chloride . . . ) aqueous and non-aqueous vehicles (e.g. water, sesame oil, cottonseed oil, soybean oil, castor oil, almond oil, oily esters, ethyl alcohol or fractionated vegetable oils, propylene glycol, DMSO, THF, 2-pyrrolidone, N-methylpyrrolidinone, N-vinylpyrrolidinone . . . ).

Alternatively, the active ingredient may be in dry form such as a powder, crystalline or freeze-dried solid for constitution with a suitable vehicle. The preparation of suitable parenteral formulations under sterile conditions is readily accomplished by standard pharmaceutical techniques well known to those skilled in the art.

As indicated, the compound of the present invention can be administered intranasally or by inhalation and is conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, (for example from Ineos Fluor), carbon dioxide or other suitable gas. In the case of a pressurised aerosol, the dosage unit may be determined by providing a valve to deliver a metered amount. The pressurised container, pump, spray or nebuliser may contain a solution or suspension of the active compound. Capsules and cartridges (made, for example, from gelatin) for use in an inhaler or insufflator may be formulated to contain a powder mix of the compound and a suitable powder base such as lactose or starch. For compositions suitable and/or adapted for inhaled administration, it is preferred that the compound or salt of formula (I) is in a particle-size-reduced form, and more preferably the size-reduced form is obtained or obtainable by micronisation. The preferable particle size of the size-reduced (e.g. micronised) compound or salt or solvate is defined by a D50 value of about 0.5 to about 50 microns (for example as measured using laser diffraction).

Alternatively, the compound of the present invention can be administered in the form of a suppository or pessary, or it may be applied topically in the form of a gel, hydrogel, lotion, solution, cream, ointment or dusting powder. The compound of the present invention may also be dermally or transdermally administered, for example, by the use of a skin patch. They may also be administered by the pulmonary or rectal routes. It may also be administered by the ocular route. For ophthalmic use, the compound can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, it may be formulated in an ointment such as petrolatum.

For topical application to the skin, the agent of the present invention can be formulated as a suitable ointment containing the active compound suspended or dissolved in, for example, a mixture with one or more of the following: mineral oil, liquid petrolatum, white petrolatum, propylene glycol, polyoxyethylene, polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Typically, a physician will determine the actual dosage which will be most suitable for an individual subject. The specific dose level and frequency of dosage for any particular individual may be varied and will depend upon a variety of factors including the activity of the specific compound employed and length of action of that compound, the age, body weight, general health, sex, diet, mode and time of administration, rate of excretion, drug combination, the severity of the particular condition, and the individual undergoing therapy. The above defined compound may be administered to a subject for its use in the treatment of Cannabinoids-Related Disorders at any dose suitable for obtaining a therapeutic effect.

For oral and parenteral administration to humans, the daily dosage level of the agent may be in single or divided doses.

A proposed range of dose of the compound according to the present invention for administration to a human (of approximately 70 kg body weight) is, including but not limited to 1 µg to 1000 mg, more typically 1 µg to 500 mg, more typically 1 µg to 100 mg, more typically 1 µg to 50 mg, more typically 1 µg to 10 mg, more typically 1 µg to 5 mg, more typically 1 µg to 1 mg, more typically 1 µg to 600 µg, more typically 1 µg to 200 µg, more typically 1 µg to 100 µg, more typically 1 µg to 60 µg, more typically 10 µg to 1000 mg, more typically 10 µg to 500 mg, more typically 10 µg to 100 mg, more typically 10 µg to 50 mg, more typically 10 µg to 10 mg, more typically 10 µg to 5 mg, more typically 10 µg to 1 mg, more typically 10 µg to 600 µg, more typically 10 µg to 200 µg, more typically 10 µg to 100 µg, more typically 20 µg to 1000 mg, more typically 20 µg to 600 mg, more typically 20 µg to 200 mg, more typically 20 µg to 60 mg, more typically 20 µg to 20 mg, more typically 20 µg to 6 mg, more typically 20 µg to 2 mg, more typically 20 µg to 600 µg, more typically 20 µg to 200 µg of the active ingredient per unit dose, expressed as the weight of free acid. The unit dose may be administered, for example, 1 to 4 times per day.

The dose will depend on the route of administration. It will be appreciated that it may be necessary to make routine variations to the dosage depending on the age and weight of the patient as well as the severity of the condition. The dosage will also depend on the route of administration. The precise dose and route of administration will ultimately be at the discretion of the attendant physician or veterinarian.

A "suitable dose", an "effective amount" of the compound of the invention refers to the effective amount sufficient to prevent, reduce, eliminate, control, treat or inhibit a Cannabinoids-Related Disorder. The term "controlling" is intended to refer to all processes wherein there may be a slowing, interrupting, arresting, or stopping the progression of the diseases and conditions described herein, but does not necessarily indicate a total elimination of all disease and condition symptoms. The doses used for the administration can be adapted as a function of various parameters, in particular as a function of the mode of administration used, of the relevant pathology, or alternatively of the desired duration of treatment. Naturally, the form of the pharmaceutical composition, the route of administration, the dosage and the regimen naturally depend on the condition to be treated, the severity of the illness, the age, weight, and sex of the subject, etc. The ranges of effective doses provided below are not intended to limit the invention and represent preferred dose ranges. However, the preferred dose can be tailored to the individual subject, as is understood and determinable by one of skill in the art, without undue experimentation.

The invention also concerns a method of treating Cannabinoids-Related Disorders in a subject in need thereof comprising the administration of an effective amount of the compound of Formula (I):

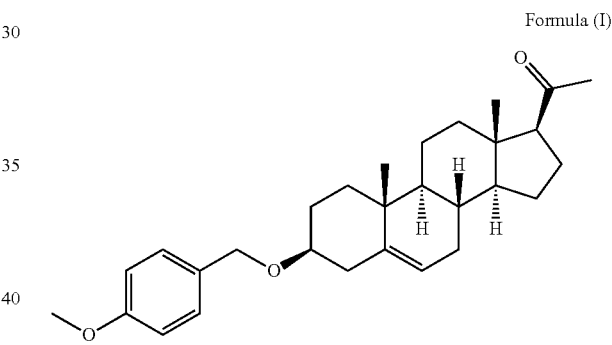

Formula (I)

to said patient.

All the embodiment disclosed above are encompassed in this aspect.

In another aspect, the present invention relates to the use of the compound of Formula (I):

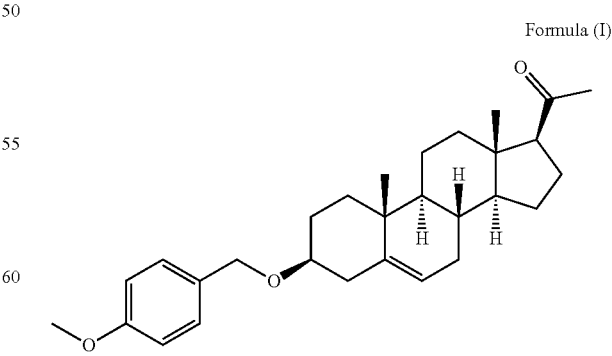

Formula (I)

for the treatment of a Cannabinoids-Related Disorder.

All the embodiment disclosed above are encompassed in this aspect.

In a further embodiment, the present invention relates to the use of the compound of Formula (I):

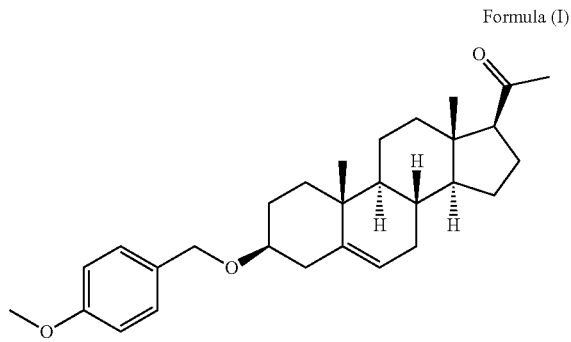

Formula (I)

for the manufacture of a pharmaceutical preparation for the treatment of a Cannabinoids-Related Disorder.

All the embodiment disclosed above are encompassed in this aspect.

EXAMPLES

Example 1: Synthesis, Preparation and Formulation of 3pMBP

3β-(4-methoxybenzyloxy)pregn-5-en-20-one (3pMBP) is a chemical entity containing 7 chiral centers 3S, 8S, 9S, 10R, 13S, 14S, 17S as described in Formula (I):

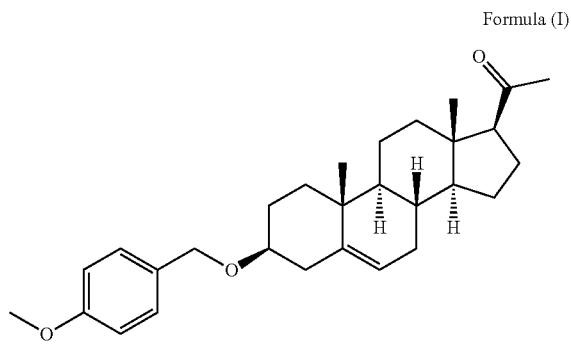

Formula (I)

The stereochemical configuration at these centers is identical to those of the starting material pregnenolone.

Preparation of 3β-(4-methoxybenzyloxy)pregn-5-en-20-one (3pMBP)

Preparation of 3pMBP is described in FIG. 1 and below

Stage 1: Preparation of the Compound of Formula (IV): (3S, 8S, 9S, 10R, 13S, 14S, 17S)-10,13-dimethyl-17-(2-methyl-1,3-dioxolan-2-yl)-2,3,4,7,8,9,10,11,12,13,14,15, 16,17-tetradecahydro-1H-cyclopenta[a]phenanthren-3-ol Stage 1 was carried out in one batch. Ethylene glycol (11.676 kg), pregnenolone (6.992 kg,) and para-toluenesulfonic acid (0.840 kg, 4.42 mol, 0.2 equiv.) were charged in a reactor. The reaction mixture was stirred at a temperature between 15° C. and 25° C. for 25 min. Triethylorthoformate (20.939 kg) was added in three portions and the mixture was stirred for at least 1 hour at a temperature between 15° C. and 25° C. Once completed, the reaction mixture was collected and poured slowly on a sodium bicarbonate solution (2.943 kg in 35.5 l of water) between 0° C. and 10° C. At the end of the addition, the reaction mixture was stirred between 0° C. and 10° C. for 1 h, then the reaction mixture was filtered and washed with water (12 l). The filtrate was also washed with 2-propanol (12 l) and dried under vacuum under a nitrogen flow. The dried solid was collected and charged in a reactor with 2-propanol (35 l). The slurry was heated at reflux for 2 h. The reaction mixture was cooled to room temperature and stirred at room temperature for 12 h. The reaction mixture was cooled between 0° C. and 10° C. then stirred for 2 h. The solid was filtered and washed with 2-propanol (12 l) then dried under vacuum under a nitrogen flow. Compound of Formula (IV) (8.031 kg) was obtained in 100.8% yield (uncorrected yield).

Stage 2: Preparation of Compound of Formula (II): 2-(3S, 8S, 9S, 10R, 13S, 14S, 17S)-3-((4-methoxybenzyl)oxy)-10,13-dimethyl-2,3,4,7,8,9,10,11,12,13,14,15,16,17-tetradecahydro-1H-cyclopenta[a]phenanthren-17-yl)-2-methyl-1,3-dioxolane Compound of Formula (IV) (3.460 kg) and tetrahydrofuran (THF) (69 l) were charged in a reactor. The reaction mixture was stirred at a temperature between 20° C. and 25° C. for 80 minutes. The reaction mixture was filtered and the solution of compound of Formula (IV) in THF was charged in a reactor. t-BuOK (2.835 kg) was added portionwise to a solution of Compound of Formula (IV) in THF at a temperature between 20° C. and 25° C. At the end of the addition, para-methoxybenzylchloride Formula (III) (2.832 kg) and THF (4 l) were added to the reaction mixture via an addition funnel. The reaction mixture was heated between 38° C. and 42° C. TBAI (1.555 kg) was charged portionwise to the reaction mixture at a temperature between 38° C. and 42° C. The reaction mixture was heated between 55° C. and 60° C. for 16 h30.

Once completed, the reaction mixture was concentrated under vacuum in order to distillate between 34 l and 36 l of THF. The reaction mixture was then cooled to room temperature.

Water (52 l) was charged in the reactor then cooled down between 0° C. and 10° C. The reaction mixture was poured onto water carefully while maintaining the temperature between 0° C. and 10° C. At the end of the addition, the reaction mixture was stirred for 1 h50 between 0° C. and 10° C. The reaction mixture was filtered and washed with water (13 l). The filtrate was washed with acetonitrile (13.5 l) and the solid was dried under vacuum under a nitrogen flow for 4 days.

The solid was collected and charged in a reactor with acetonitrile (13 l). The mixture was heated at reflux for 4 h. Additional acetonitrile (11 l) was charged in the reactor and heated at reflux until a clear solution was obtained. The reaction mixture was cooled to room temperature and stirred at room temperature for 14 h. The reaction mixture was cooled between 0° C. and 10° C., stirred for 45 minutes between 0° C. and 10° C. then filtered. Acetonitrile (10.5 l) was charged in the reactor, cooled between 0° C. and 10° C., then added onto the filter to wash the filtrate and the solid was dried under vacuum under a nitrogen flow for 21 h. Compound of Formula (II) (2.449 kg) was obtained in 59.2% yield.

Stage 3: Preparation of Compound of Formula (I): 3pMBP

Compound of Formula (II) (2.448 kg) and dichloromethane (10 l) were charged in a reactor. The solution was stirred for 20 minutes. Hydrochloric acid 1 M (4.9 l) was added to the solution between 15° C. and 25° C. The reaction mixture was stirred until completion between 15° C. and 25° C. Dichloromethane (8 l) was added (to fully dissolve any precipitate) and phases were allowed to separate. Organic layer was washed with water (5 l) twice. Organic layer was collected and charged with 2-propanol (24.5 l) in the reactor between 15° C. and 25° C. The reaction mixture was concentrated under vacuum with a temperature below 40° C. Once complete, the reaction mixture was heated up to reflux. 2-propanol (40 l) was added until a clear solution was observed. The reaction mixture was cooled to room temperature and stirred at room temperature for 12 h. The reaction mixture was cooled between 0° C. and 10° C., stirred for 1 h between 0° C. and 10° C. The solid was filtered and washed with 2-propanol (5 l) then dried under vacuum equipped with a nitrogen flow rate while heating the filter between 35° C. and 45° C. for 20 h. Compound of Formula (I) (1.907 kg) was obtained in 85.8% yield.

Pharmaceutical Composition

3β-(4-methoxybenzyloxy)pregn-5-en-20-one can be formulated as capsule dosage form containing solution of 3β-(4-methoxybenzyloxy)pregn-5-en-20-one in corn oil. The composition of this dosage form is described in Table 1.

The present invention provides an example for the preparation of soft gelatin capsules containing respectively a 20-μg, 0.2-mg and 2-mg solution of 3β-(4-methoxybenzyloxy)pregn-5-en-20-one in corn oil.

The steps composing the manufacturing process can be briefly described as follow:

1. 3β-(4-methoxybenzyloxy)pregn-5-en-20-one was stirred in corn oil until complete dissolution.

2. Then 3β-(4-methoxybenzyloxy)pregn-5-en-20-one solution of step 1 was filled into a soft gelatin capsule.

All excipients are compliant with current in force European pharmacopoeia (Ph. Eur.) monographs and United States Pharmacopoeial-National Formulary (USP-NF) monographs.

TABLE 1

Composition of 3β-(4-methoxybenzyloxy)pregn-5-en-20-one soft gelatin capsules

|  | 0.02 mg capsule | 0.20 mg capsule | 2.00 mg capsule |
| --- | --- | --- | --- |
| 3pMBP | 0.020 mg | 0.200 mg | 2.000 mg |
| Corn Oil | 96.980 mg | 969.800 mg | 969.000 mg |
| Titanium Dioxide | 1.04 mg | 5.29 mg | 5.29 mg |
| Glycerol 85% | 21.61 mg | 134.77 mg | 134.77 mg |
| Gelatin, | 47.79 mg | 232.02 mg | 232.02 mg |
| Total weight | 167.44 mg | 1342.08 mg | 1342.08 mg |

Example 2: Specific Inhibition of the Activity of the CB1 Receptor by 3pMBP

The understanding of the effects of the compound of the present invention, 3pMBP, on the activity of the CB1 receptor has been pursued by studying the effects of 3pMBP on the following cellular effects induced by the activation of the CB1 receptor by THC. The specificity of the effects of 3pMBP on the CB1 receptor was studied by analysing the effects of this compound on the binding of other 85 receptors.

Materials and Methods

Effect of 3pMBP on THC-Induced Increase in MAPK Phosphorylation:

The aim of this study was to assess the effects of 3pMBP on the increase in the phosphorylation of Erk1/2MAPK, commonly called MAPK (Mitogen-Activated Protein Kinases), induced by THC administration in Human embryonic kidney 293 (HEK-293) cells stably or transitorily transfected with the human CB1 (hCB1) receptor.

HEK-293 cells were chosen because they do not express endogenous CB1 receptors, they can be easily transfected and have been previously used in experiments studying the in vitro activity of the CB1 receptor (Shore et al., 2014) and in experiments showing that pregnenolone is able to inhibit THC-induced phosphorylation of MAPK (Vallée et al. 2014). The effect of 3pMBP at three doses (1 nM, 10 nM and 100 nM, dissolved in acetonitrile 0.01%) was tested on the effect of THC at 1 μM (dissolved in EtOH $6.2^{e-4}$%, Experiment 1) and 10 μM (dissolved in EtOH $6.2^{e-3}$%, Experiment 2) on the phosphorylation of MAPK. The difference in the concentrations of THC used in the two experiments is related to the different efficiency of transfection of hCB1 cDNA plasmid, which is stable in Experiment 1 and transient in Experiment 2. THC and 3pMBP treatment were concomitant and lasted 5 min.

MAPK phosphorylation (P-Erk1/2MAPK proteins) was measured by western blot. In experiment 1 the mitochondrial marker CoxIV and in experiment 2 the un-phosphorylated MAPK proteins were used as loading controls. The P-MAPK/CoxIV and P-MAPK/MAPK ratios were calculated and the data expressed as % of vehicle-treated cells.

Effect of 3pMBP on THC-Induced Decrease in cAMP

The aim of this study was to assess the effects of 3pMBP on the decrease in cAMP induced by THC administration in Chinese Hamster Ovary (CHO) cells stably expressing the human CB1 receptor CHO-hCB1.

CHO-hCB1 cells were chosen in these experiments because they do not endogenously express the CB1 receptor and have been previously used in experiments studying the effects of CB1 agonists (Rinaldi-Carmona, 1996), including THC, on cAMP and P-MAPK.

The effects of 3pMBP at four doses (1 nM, 10 nM, 100 nM and 1 μM, dissolved in N,N-Dimethylformamide 0.01%) were tested against a dose response function of THC (0.3 nM, 1 nM, 3 nM, 10 nM, 30 nM, 100 nM and 300 nM, dissolved in ethanol 0.0063%).

CHO-CB1-C2 cells were treated by concomitantly adding THC and the test compound for 45 minutes. Forskolin (2.5 μM) was also simultaneously added in all the conditions tested to sustain cAMP basal level. At the end of the treatment, cells were lysed to proceed with the cAMP quantification. All measures were performed in triplicates in one experiment.

The quantitative determination of cAMP was performed through a competitive fluorescence immunoassay. Data were expressed as % of Delta Fluorescence (Delta F) that was calculated as follows: Delta F %=(Sample Fluorescence−Negative control Fluorescence)/Negative control Fluorescence.

Effect of 3pMBP on THC-Induced Decrease in Cellular Respiration

The aim of this study was to test the effect of 3pMBP on the inhibition of cellular respiration induced by THC (1 μM) in HEK-293 cells transiently transfected with the human CB1 receptors (hCB1).

HEK-293 cells transiently transfected with the hCB1 expressing plasmid were first treated with 3pMBP (0, 1, 10 and 100 nM dissolved in acetonitrile 0.01%). After 15 min of incubation, THC (0, 1 µM, dissolved in EtOH 0.0034%) was added in the culture dishes for 30 minutes.

Cellular respiration was measured in a calibrated oxygraph equipped with a Clark electrode. Oxygen consumption (OC) rate was used to measure cellular respiration. The effects of THC, in absence and in presence of 3pMBP, on OC rate were expressed as percentages of the baseline OC of the cell treated with the vehicle of 3pMBP and the vehicle of THC of the same experiment. 10 independent experiments were performed to obtain a n=10 per experimental condition. Each experiment had a n=5 containing n=1 per experimental group.

Binding Selectivity of 3pMBP In Vitro:

This series of assays aimed to evaluate the binding specificity of 3pMBP comparing it to the profile of pregnenolone.

The potential ability of 3pMBP and pregnenolone, at a concentration of 10 PM, to displace the binding of ligands of 85 receptors (CEREP High-throughput profile+4 steroid receptors+Cannabinoid type 2 receptor) was tested. The CEREP High-throughput profile consists of a broad collection of 80 transmembrane and soluble receptors, ion channels and G-Protein coupled receptors. It has been specifically designed to provide information to prioritize the most promising compounds in hit-to-lead selection process. The androgen, estrogen, progesterone and PXR receptors and then Cannabinoid type 2 receptor were added to this assay in order to better tailor the assay to 3pMBP completing the spectrum of steroid receptors already contained in the CEREP high-throughput profile.

Results

Figure 2:
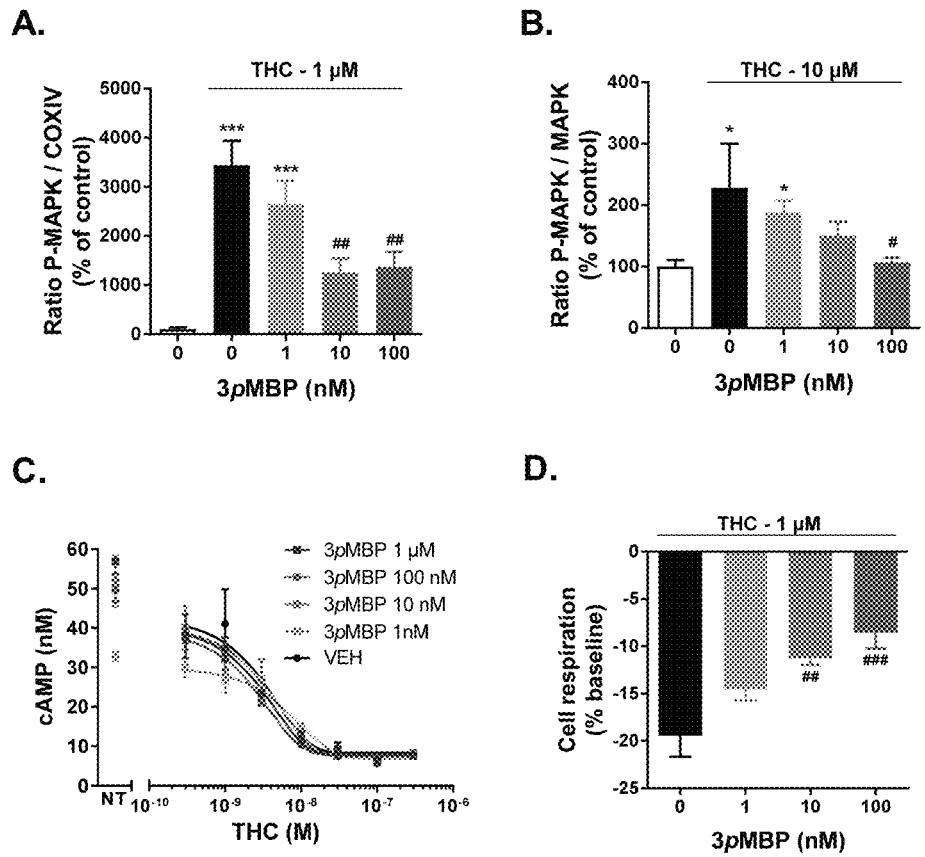
FIG. 2: In vitro effects of 3pMBP on THC-induced modifications of CB1-mediated signaling and cellular activities.

3pMBP has a profile similar to the eCB1-SSi pregnenolone. 3pMBP inhibits THC-induced increase in MAPK phosphorylation (FIGS. 2A and 2B) and THC-induced decrease in cellular respiration (IC50=1.2-11 nM) in HEK-293 cells stably or transitorily transfected with hCB1 (FIG. 2D).

In contrast 3pMBP did not inhibit THC-induced decrease in cAMP in CHO cells stably expressing the human CB1 receptor CHO-hCB1 (FIG. 2C).

In addition, 3pMBP (10 µM) did not modify the binding of any of the 85 receptors that were tested in vitro using the CEREP High-throughput profile, including the major steroid receptors, the PXR receptors and the CB1 and the CB2 receptors. In this respect 3pMBP was more selective than pregnenolone (10 µM), which displaced (>80%) the binding of the glucocorticoid, androgen and progesterone receptors and to a lesser extent (>40%) the binding of the central and peripheral benzodiazepine receptors.

The effects of 3pMBP are summarized in the table below:

Conclusion

Hence, 3pMBP in vitro acts as a Signaling-Specific inhibitor of the CB1 (CB1-SSi). Thus, 3pMBP, in cell lines expressing the human CB1 receptor (hCB1) inhibited THC-induced increase in MAPK (mitogen-activated protein kinase) phosphorylation and THC-induced decreases in cellular respiration. In contrast, 3pMBP did not inhibit THC-induced decreases in cAMP (cyclic adenosine monophosphate).

Furthermore, 3pMBP in vitro is more selective than the endogenous signaling specific inhibitor pregnenolone. Indeed, pregnenolone (10 µM) displaces the binding (>80%) of the progesterone, glucocorticoid and androgen receptors, as well as the binding of the benzodiazepine receptors (>40%). 3pMBP (10 µM) did not modify the binding of these receptors or of any of the other receptors (85 in total) that were studied using the CEREP high-throughput profile.

Example 3: Preclinical Evaluation of 3pMBP as a Treatment of Cannabinoids-Related Disorders In the following preclinical studies, 3pMBP has been solubilized in corn oil, a long chain triglyceride vegetable oil which can be safely used in humans. This lipid formulation has been administered per os by gavage as a liquid.

The activation of the CB1 receptor can produce Cannabinoids-Related Disorders and its associated adverse consequences by two complementary effects:
1. The unconditioned pharmacodynamic effects of cannabinoids that include profound cognitive, motivational and behavioral impairments. These three effects may synergistically produce serious consequences for different type of Cannabinoids-Related disorders. They are notably responsible of: a. Impaired social relationships and lower life satisfaction; b. Poorer educational outcomes, lower income, greater welfare dependence and unemployment, in particular for the most prone population (14-25 years of age); c. psychiatric disorders including but not limited to depression, anxiety and psychosis; and d. Resistance to engage in psychological treatments;
2. The conditioned effects of cannabinoids leading to development of cannabinoids seeking, regular use and ultimately to cannabinoids dependence. The ability of cannabinoids to condition behavior, which leads to cannabinoids addiction, makes the discontinuation of cannabinoids use difficult and facilitates relapse after a period of abstinence, resulting in continuous exposure to cannabinoids' adverse effects.

TABLE 2

In vitro evaluation of the mechanism of action of 3pMBP

| Effects of 3pMBP on: | Test system | ID50 | ID100 | % inhibition |
|---|---|---|---|---|
| THC-induced increase in MAPK phosphorylation in cells stably expressing the hCB1 | HEK-293 | 1.2 nM | 10 nM | 60 |
| THC-induced increase in MAPK phosphorylation in cells transiently expressing the hCB1 | HEK-293 | 11 nM | 100 nM | 100 |
| THC-induced decrease in cAMP | CHO | >1 µM | — | NA |
| THC-induced decrease in cellular respiration | HEK-293 | 8 nM | 100 nM | 57 |
| CEREP High-throughput binding profile (85 receptors) | Receptor binding | >10 µM | — | NA |

NA = Not Analyzed because no effect was found

Based on the previous observations, an ideal pharmacological treatment for Cannabinoids-Related Disorders should be able to:
1. Antagonize a large spectrum of unconditioned effects of cannabinoids, in order to reduce the negative impact of cannabinoids use on brain functioning and behavior.
2. Facilitate the reduction of cannabinoids use and decrease relapse to cannabinoids use after discontinuation, in order to decrease the exposure of the brain to cannabinoids and its negative consequences.

These two combined effects, creating a positive feedforward loop (decrease of cannabinoids effects and decrease in the amount of the cannabinoids taken), should provide a powerful tool to treat the different Cannabinoids-Related Disorders.

Taking into account these considerations, the preclinical evaluation of the potential of 3pMBP as a treatment of Cannabinoids-Related Disorders was performed by studying:
1. Several behavioral models that reproduce the unconditioned effects of CB1 agonists in cannabinoids users. For these studies the active principle of *cannabis* THC was used because it is the most used cannabinoids in humans.
2. Several behavioral models (in mice and non-human primates) evaluating the ability of THC and synthetic cannabinoids to condition behavior and induce dependence. 1. Inhibition by 3pMBP of the Unconditioned Effects of THC The inhibition by the oral administration of 3pMBP of the hereinafter described unconditioned behavioral and neurochemical effects of THC related to Cannabinoids-Related Disorders was studied:
a. THC-induced increase in food intake;
b. THC-induced increase in psychomotor stimulation;
c. THC-induced impairment of pre-pulse inhibition;
d. THC-induced memory impairments;
e. THC-induced impairment of social interaction;
f. THC-induced impairment of reality testing;
g. THC-induce catalepsy;
h. THC-induced gaping behavior;
i. THC-induced dopamine release in the nucleus accumbens.

a. THC-Induced Increase in Food Intake

These experiments aimed to evaluate the ability of 3pMBP to inhibit the increase in food intake induced by THC-administration in mice. This behavior was chosen because in *cannabis* users there is a disruption of feeding behavior with a propensity to hyperphagia and preference for palatable food just after drug consumption (Kirkham, 2005).

Materials and Methods

The effects of THC on food intake were studied using the fasting-refeeding model (Bellochio et al., 2010) in $CB1^{f/f}$ male mice. The effect of 3pMBP at three doses (5, 15 and 50 μg/kg) was tested on the increase in food intake induced by THC (1 mg/kg; ip) in 24-hour food deprived mice that were refed 30 minutes post-THC. Food intake was measured for one hour. Independent groups of animals (at least n=8 per group) were used for each treatment condition. 3pMBP was administered three hours before the administration of THC.

Results

As described in FIG. 3A, 3pMBP inhibits ($ID_{50} \approx 15$ and $ID_{100} \approx 50$ μg/kg) the increase in food intake induced by THC (1 mg/kg) in mice.

b. TIC-Induced Increase in Psychomotor Stimulation

These experiments aimed to evaluate the ability of 3pMBP to inhibit the increase in psychomotor stimulation induced by THC administration in mice. This behavior was chosen because it is considered as a surrogate of psychotic-like symptoms that can be triggered by *cannabis* use (Wiley et al., 2008; DSM $5^{TH}$ ed., 2013).

Materials and Methods

THC-induced psychomotor stimulation was studied in C57BL/6N male mice by measuring locomotor activity in an open field with a square-patterned floor. Locomotion was evaluated 45 minutes post-THC for 5 minutes by counting the number of squares crossed and expressed as percentage of vehicle-treated controls.

The effect of 3pMBP at five doses (0.00015, 0.0005, 0.0015, 0.015 and 0.15 mg/kg) was tested on the increase in locomotor activity induced by THC (0.3 mg/kg). Independent groups of animals (at least n=9 per group) were used for each dose of 3pMBP. 3pMBP was administered three hours before the administration of THC.

Results

3pMBP inhibits ($ID_{50} \approx 0.0004$ and $ID_{100} \approx 0.0015$ mg/kg) the psychomotor stimulation induced by THC (0.3 mg/kg) in mice (FIG. 3B).

c. THC-induced Impairment of Pre-Pulse Inhibition

These experiments aimed to evaluate the ability of 3pMBP to inhibit the impairment of sensory gating induced by THC administration in mice as studied by the prepulse inhibition (PPI) test. This behavior was chosen because it is a model of the impairment of sensory-motor gating observed in psychosis (DSM $5^{th}$ ed., 2013; Kedzior et al. 2006) which has been shown to be induced by THC (Nagai, 2006).

Materials and Methods

The effect of 3pMBP at five doses (0.0005, 0.0015, 0.015, 0.03 and 0.05 mg/kg) was tested on the impairment in PPI induced by THC (10 mg/kg) in C57BL/6N male mice. 3pMBP was administered three hours before the administration of THC.

PPI was measured using automated PPI cages allowing the automatic PPI protocol delivery and the recording of the animal's startle reactions. Each mouse (at least n=8 per group) was placed in the PPI test 60 minutes post-THC for 45 minutes.

The PPI test included different types of trials consisting in the presentation of either the background noise, the startle stimulus (S; 120 dB) alone, one of the prepulse (73 dB, 76 dB or 82 dB) stimuli alone or a combination of one of each prepulse stimulus followed by the startle stimulus (PPI-S). The startle response following the pulse presentation was recorded and an index of PPI was calculated (% PPI=100× (S−PPI-S)/S).

Results

3pMBP inhibits ($ID_{50} \approx 0.005$ and $ID_{100} \approx 0.015$ mg/kg) the impairment of pre-pulse inhibition induced by THC (10 mg/kg) in mice. FIG. 3C show the effect of 3pMBP with a prepulse of 82 dB.

d. Effects of 3pMBP on THC-Induced Memory Impairments

In these experiments the effects of 3pMBP on the impairment induced by THC on two memory tests were studied: a. working memory and b. long-term memory. Working memory is the ability to temporarily store and process information. It is required to carry out everyday life activities such as holding a conversation, reasoning, reading comprehension. Working memory deficit is one of the core cognitive symptoms in psychosis that is not improved by current antipsychotics (Pratt et al., 2012). Working memory impairment is also a typical consequence of the acute administration of THC both in humans and in animals (D'Souza, 2007). Long-term memory is the ability to store learned information in a stable memory compartment that allows to recall it long time after the learning occurred. An impairment of long-term memory is also a typical effect of THC administration.

Material and Methods

Impairment of Working Memory Induced by THC

In mice, working memory can be evaluated in the delayed matching-to-place version of the Morris water maze, a spatial memory task in which animals need to process new and previously acquired information to find the location of a hidden escape platform.

In mice, the acute administration of THC (5 mg/kg) impairs working memory in this task (Busquets-Garcia et al., 2017).

The apparatus consisted in a white circular pool (150 cm of diameter and 60 cm high) placed in the middle of the experimental room with a light intensity from 90 to 100 lux. The pool was filled with water (19-21° C.) rendered opaque using a nontoxic inodorous white cosmetic paint. A white 14-cm diameter platform was hidden 1 cm below the water surface. This behavioral test consisted of three phases: habituation, training and testing. During the habituation phase the animals were placed once in the pool for 90 seconds and then let on the platform for 30 seconds to get used to the experimental conditions and to decrease their stress during the training and the test. Once habituated, mice underwent training. Different shape pictures posted on the walls of the room served as spatial cues. Each training session (one per day) consisted in four trials. At each trial the mouse was placed in the water, face to the wall of the pool, and then left to swim until it reached the hidden platform. If the mouse did not reach the platform within 90 seconds, it was guided to it. The mouse then stayed on the platform for 30 seconds (inter-trial interval). The starting locations were the same for the first and the fourth trials, but different for the other ones. The position of the platform was changed every day, so that at the first trial of each session, the mouse always found it by chance. Training sessions are repeated until the mice performed a significant decrease in the latency to reach the platform between the first trial and each of the 3 following trials for three consecutive days. Training lasted 8 to 12 days. After training, mice received the pharmacological treatments and then performed a single test session using the same protocol as training sessions (i.e. 4 trials, inter-trial intervals of 30 seconds, cut-off at 90 seconds).

The working memory performance at the test session was measured by calculation of the time saving ratio using the following formula: saving ratio=(escape latency trial 1−escape latency trial 4)/(escape latency trial 1+escape latency trial 4).

Mice were administered with THC (5 mg/kg, ip) or its vehicle 30 minutes before the test session. 3pMBP (0.015; 0.15 or 0.45 mg/kg, per os by oral gavage) or its vehicle was administered 3 hours before THC or its vehicle administration.

Impairment of Long-Term Memory Induced by THC.

In mice long-term memory can be evaluated using the object recognition test in which the memory of one specific object is evaluated 24 h later. For this specific experiment, CD1-SWISS male mice received an acute per os administration of 3pMBP (0.005 mg/kg) or corn oil (5 ml/kg) vehicle followed 3 hours later by an intraperitoneal (ip) injection of THC (6 mg/kg; 10 ml/kg). Ten minutes before THC injection, mice were allowed to explore 2 identical objects in an "L"-shaped maze. The day after, one object was replaced by a novel one. According to the spontaneous novelty preference, mice explore longer novel objects (Ennaceur, 2010). The comparison of the time spent exploring the familiar and the novel objects is used as an index of discrimination between familiarity and novelty. Therefore, this parameter is used to evaluate object recognition performances.

Results

3pMBP fully inhibits THC-induced object recognition impairment (FIG. 4B) at 0.005 mg/kg with an ID50 that was <0.005 mg/kg. Similarly, 3pMBP administered at 0.015; 0.15 or 0.45 mg/kg dose-dependently blocks the impairment of working memory performances induced by THC (5 mg/kg) with an ID100 of 0.15 mg/kg (FIG. 4A).

e. Effects of 3pMBP on THC-Induced Impairment of Social Interaction

Social withdrawal in psychosis is defined as the indifference or lack of desire to have social interaction (Wilson and Koenig, 2014). Social interaction can be evaluated in mice by measuring their spontaneous preference for the encounter with a congener as compared to non-social encounter. In this paradigm, the acute administration of THC (3 mg/kg) reduces social preference (Busquets-Garcia et al., 2017; FIG. 4C), providing a reliable model of the social withdrawal endophenotype in psychosis.

Material and Methods

Mice were tested in an open field (35×35 cm) with two plastic containers (plastic cylinders of 8 cm diameter with holes for odor interaction) placed at two opposite corners, one of them hosting a mouse (8- to 10-week-old adult male C57BL/6-N), while the other container remained empty. In each corner were defined the 'social' and 'non-social' zones as an 8-cm area surrounding the containers. For each experimental group, the position of the container with the mouse was counterbalanced. The experimental mouse was placed in the center of the open field to explore for 5 minutes, filmed by a camera. The time spent in both zones was counted considering that the animal is in one zone when all its four paws are inside the drawn lines. Social index was calculated as follow:

Social index=Time spent in the "social zone"/Total time spent in both zones.

Mice were administered with THC (3 mg/kg, ip) or its vehicle 2 hours before entering the open field. 3pMBP (0.005; 0.015; 0.05 mg/kg, per os in corn oil) or its vehicle was administered 3 hours before THC or its vehicle.

Results

3pMBP administered at 0.005; 0.015 or 0.05 mg/kg, dose-dependently blocks the reduction of social interaction induced by THC with an ID100 at 0.015 mg/kg (FIG. 4C).

f. THC-Induced Impairment of Reality Testing

Alterations in the mental representation of stimuli leading to mismatches between perceptions and reality are key features of positive symptoms of psychotic states (Busquets-Garcia et al., 2017). In rodents, the 'reality testing' task assesses the potential mismatch between internal representation of a stimulus (odor or taste) and the reality they predict.

This test is based on the conditioned aversion paradigm. Two stimuli of equal valence, typically a taste and an odor, are first presented simultaneously in a repeated manner (6 times). One of the stimuli, for instance the odor, is then associated with a noxious event (i.e. LiCl-induced gastric malaise). After conditioning, mice show a specific aversion for the stimulus paired with the noxious event (i.e. the odor)

but not for the neutral stimulus (i.e. the taste) although the odor and the taste were previously presented together. These responses suggest that mice built specific representations of each of the stimuli. However, psychotogenic drugs including MK-801, amphetamine and THC lead to aversion for both stimuli including the one that was not conditioned with the noxious event (mediated aversion). This effect suggests that psychotogenic drugs induce an inaccurate representation of the "neutral" stimulus. These alterations are reversed by the atypical antipsychotic risperdone (Busquets-Garcia et al., 2017). Therefore, impairment of 'reality-testing' induced by THC as well as other psychotogenic drugs in mice shows both face and predictive validity for the investigation of positive psychotic symptoms.

Material and Methods.

The realty-testing consists in four phases with different pairings (a pairing refers to the association of two stimuli at a time): habituation (3 days), preconditioning (6 pairings odor/taste, 12 days), conditioning (i.e. 3 pairings odor/injection of an agent inducing malaise, LiCl, 6 days), recovery day (1 day with water) and finally the tests (mediated aversion and direct aversion tests).

Mice were water deprived for 24 hours before starting the habituation that consisted in 1-hour access to water per day during 3 days in order to get used to receive liquid every day for 1 hour, and thus reach a constant consumption over the protocol. This was followed by the preconditioning phase in which the mice were given 1-hour access per day to a mixed solution (O1T1) with one odor (either almond or banana, O1) and one taste (either maltodextrine or sucrose, T1) in water. On day 2, mice received 1-hour access to the solution with the odor and taste not given the previous day (O2T2). After 6 pairings of O1T1 and O2T2 (12 days), the conditioning phase was started.

At the first day of conditioning, mice were given 1-hour access to odorized water (O1) directly followed by intraperitoneal injection of saline. The following day, mice were given access to the second odorized water (O2) directly followed by an intraperitoneal injection of LiCl (0.3 M) at a volume of 10 ml/kg to create gastric discomfort. After 3 pairings of O1/saline and O2/LiCl (6 days), mice were given a recovery day with 1-hour access to water.

The next day, mediated aversion was assessed by performing a two-choice test with two bottles of water containing one of the two tastes: the taste paired with the odor associated with LiCl injection (T2) called C+; or the taste paired with the other odor that was associated with the saline injection (T1) called C−. In this test, the appearance of mediated aversion is signaled by a decrease of the consumption of water containing the taste paired with the odor that had been previously paired with LiCl (T2, C+) as compared to the water containing the other taste that was associated with the odor that was never paired with LiCl (T1, C−). The tests results were expressed by the aversive index as follows:

Aversive index=(Consumption of C−−Consumption of C+)/Total consumption

Mice were administered with THC (1 mg/kg, ip) or its vehicle 2 hours before the two-choice test assessing mediated aversion. 3pMBP (0.015; 0.05 mg/kg, per os) or its vehicle was administered 3 hours before THC or its vehicle.

Results

After a saline injection, animals do not show aversion to a taste that was previously associated with the odor that during conditioning acquire the property to predict the malaise induced by LiCl (FIG. 4D). This is a correct interpretation since the taste has never been directly associated with the aversive stimulus (the injection of LiCl). On the contrary THC induces aversion to the same taste, a behavioral response indicating that the animal is performing a misinterpretation of external stimuli (FIG. 4D). 3pMBP administered at 0.015 or 0.05 mg/kg fully prevents this misinterpretation induced by THC (1 mg/kg) with an ID100 at 0.015 mg/kg (FIG. 4D).

g. THC-Induced Catalepsy

These experiments aimed to evaluate the ability of 3pMBP to inhibit THC-induced catalepsy in mice. Catalepsy was studied because it can be considered as a model of the catatonic state observed in certain subjects after the use of cannabinoids drugs (Khan et al., 2016).

Material and Methods

The effects of 3pMBP at four doses (0.0015, 0.005, 0.015 or 0.05 mg/kg) in 5 ml/kg of corn oil) was studied on the catalepsy induced by THC (10 mg/kg in 10 ml/kg of 0.9% NaCl containing 2% ethanol and 3% Tween80) in C57BL6/J male mice (24.8±0.1 g, mean±SEM, at the start of the experiments), a strain that is routinely used for this type of test (Vallée et al., 2014). THC was injected 3 h00 following 3pMBP. Measuring of the catalepsy induced by THC was started 30 min after THC injection.

Catalepsy was measured by the catalepsy bar test. The forepaws of mice were placed on a bar fixed horizontally at 3.5 cm from the bench surface. The latency for moving from the bar was recorded with a cut-off time fixed at 420 s (7 min). Each mouse was submitted to a maximum of four consecutive trials. The maximum latency shown at one trial was selected as the measure of catalepsy.

Results

3pMBP inhibited (by 50%) the catalepsy induced by THC (10 mg/kg) with an ID50≈0.005 and ID100≈0.05 mg/kg (FIG. 5A).

h. THC-Induced Conditioned Gaping Behavior

THC-induced gaping was used here as a model of Cannabinoids Hyperemesis Syndrome.

Thus, although rats are incapable of vomiting, they demonstrate profound conditioned gaping reactions during re-exposure to a flavor previously paired with an emetic drug. This robust learning occurs in a single trial and with long delays (hours) between consumption of a novel flavor and the emetic treatment. Conditioned gaping reactions are consistently produced by emetic drugs and are prevented by anti-emetic drugs, indicating that they are a robust measure of malaise and nausea induced by a drug.

Material and Methods

Three days after cannulation surgery, rats were adapted to the taste reactivity chamber. Rats were individually placed in a Taste Reaction (TR) chamber with their cannulas attached to an infusion pump to infuse water into their intraoral cavity over a period of 2 min at the rate of 1 ml/min and then returned to their home cage. Rats received the first of three daily conditioning trials three days after the adaptation trial. Rats were randomly assigned to pre-treatment drug conditions; 3pMBP 0.015 mg/kg (n=8), 3pMBP 0.005 mg/kg (n=8), Vehicle 0 mg/kg (n=8). Rats received the pre-treatment drug 3 hours prior to conditioning via feeding tube. They were then placed in the TR chamber and infused with 0.1% saccharin solution for 2 min at a rate of 1 ml/min while orofacial reactions were recorded. Immediately following saccharin infusion, the rats were injected (per os) with 10 mg/kg THC or VEH and returned to their home cage. Twenty-four hour later, the rats underwent a drug free test trial where they were placed in the TR chamber and infused with 0.1% saccharin solution for 2 min at a rate of 1 ml/min and orofacial reactions were recorded.

Results

When conditioned with 10 mg/kg THC, rats gaped more during the test trial than during the conditioning trial. As can be seen in FIG. 5B, pre-treatment with both doses of 3pMBP (0.005 and 0.015 mg/kg) interfered the establishment of conditioned gaping by reducing the mean number of gaping reactions (difference between vehicle and 3pMBP 0.005 mg/kg, p=0.023, between vehicle and 3pMBP 0.015 mg/kg, p=0.029).

i. THC-Induced Dopamine Release in the Nucleus Accumbens

These experiments aimed to evaluate the ability of 3pMBP to inhibit the increase of dopamine (DA) release induced by THC in the nucleus accumbens (Nac) of freely moving rats, as measured by the microdialysis technique. DA release in the Nac was studied because it is considered the major biological substrate of the addictive properties of drugs of abuse including THC.

Materials and Methods

The effect of 3pMBP at three doses (0.005, 0.015 or 0.05 mg/kg, per os; was tested on the increase in DA release in the Nac induced by THC (1 mg/kg) in male Sprague-Dawley rats. THC was solubilized in 0.9% NaCl containing ethanol (2%) and Tween80 (2%) that was also used as control vehicle (VEH$_{THC}$) and administered intraperitoneally in a volume of 1 ml/kg.

Rats (n=5-7 per group) were implanted under anesthesia with a guide-cannula just above the shell sub-regions of the right Nac. The day of the pharmacological experiment (5-7 days after surgery), freely moving rats received one of the doses of 3pMBP or VEH$_{3pMBP}$, and the microdialysis probe was implanted into the guide-cannula that was then perfused with artificial cerebrospinal fluid. Dialysates were collected every 15 minutes. 180 minutes after the beginning of the perfusion, all animals received an injection of THC. DA outflow was then monitored for 120 minutes. The concentrations of DA in dialysate samples were analyzed by reverse-phase high-performance liquid chromatography (HPLC) coupled with electrochemical detection, as described previously (Leggio et al., 2009). DA content in each sample was expressed as the percentage of the average baseline level calculated from the three fractions preceding THC administration. The area under the curve (AUC) was calculated for each group from sampling time 0 min to 60 min after THC injection.

Results

3pMBP inhibits (ID50≈0.005 and ID$_{100}$≈0.015 mg/kg) the increase in dopamine release in the nucleus accumbens induced by 1 mg/kg of THC in rats (FIGS. 5C and 5D).

2. Inhibition by 3pMBP of the Ability of THC and CB1 Agonists to Condition Behavior and Induce Dependence The inhibition by the oral administration of 3pMBP of the hereinafter described conditioned pharmacodynamic effects of CB1 agonists and THC was studied:

a. Intravenous self-administration of the CB1 agonist WIN 55, 212-2;
b. Intravenous self-administration of THC and Reinstatement of THC-seeking.

a. Intravenous Self-Administration of the CB1 Agonist WIN 55, 212-2

These experiments aimed to evaluate in mice the ability of 3pMBP to inhibit the reinforcing effects of the CB1 agonist WIN 55,212-2 (WIN) as studied by the intravenous self-administration test, which is considered the gold standard to measure the reinforcing effects of drugs.

Materials and Methods

The effects of 3pMBP on intravenous (iv) self-administration were measured in male CD1-Swiss mice.

Before the start of the self-administration sessions, mice were implanted under anesthesia with catheters into the right jugular vein. The self-administration experiments were conducted 3 days after surgery in mouse operant chambers equipped with one "active" and one "inactive" holes. When the animal inserted its nose (nose poke) in the active hole, it received an iv infusion of WIN (12.5 µg/kg). Mice were trained under a fixed ratio 1 (FR1) schedule of reinforcement.

Two hour daily self-administration sessions were conducted 6 days per week for 19 days. Mice received corn oil vehicle (2 ml/kg) per os on day 9 and 10 to be habituated to the oral gavage procedure. On day 11, mice were randomized into two groups (n=13 per group), one received 3pMBP, the other corn oil vehicle 3 hours before the start of the self-administration session for 9 consecutive days. 3pMBP was administered at 0.005 mg/kg the first four days and at 0.015 mg/kg the remaining five days.

Results

3pMBP inhibits (ID$_{50}$≈0.005 and ID$_{100}$≈0.015 mg/kg) the intravenous self-administration of WIN 55,212-2 in mice (FIG. 6).

b. Intravenous Self-Administration of THC and Reinstatement of THC-Seeking in Non-Human Primates These experiments aimed to evaluate the ability of 3pMBP to inhibit the reinforcing effects of THC, in non-human primate (Squirrel monkeys) which is the gold standard model for studying *cannabis* addiction and relapse in animals. Two experimental models were used:

THC-mediated intravenous self-administration
THC priming-mediated reinstatement of THC seeking These two models were used because they are considered the best models to measure respectively the propensity of an individual to use *cannabis* and the liability to relapse in *cannabis* use after a period of abstinence.

Materials and Methods

For all the experiments 3pMBP was administered per os in a grape in a volume of 0.1 ml of corn oil 4 h before testing.

Four male Squirrel monkeys (*Saimiri sciureus*) were used because they are the species in which THC self-administration can be the most reliably studied.

Monkeys were trained to lever-press to get an intravenous (iv) injection of THC (4 µg/kg/injection) under a ten-response fixed-ratio schedule of drug injection (FR10, each 10th response on the lever produced an injection of THC).

Number of lever presses and number of injections per session were recorded. Response rates are calculated based on available session time for responding (i.e., timeout time is subtracted). Statistics are performed for number of injections and response rates per session using either one-way or two-way repeated measures ANOVA with the THC dose or the time as factors.

The monkeys used in the previous experiments underwent daily extinction sessions during which lever-presses led to vehicle infusions plus the visual cues previously paired with THC infusions, but not THC. After at least two extinction sessions, when responding had reached a low level, the effect of pretreatment with 3pMBP (0.0015, 0.005, and 0.015 mg/kg) or control vehicle of 3pMBP on THC priming-induced (0.04 mg/kg iv) reinstatement of THC seeking was determined. THC priming injections were given immediately before the start of the test sessions. During testing, lever-presses (FR10) continued to produce only vehicle injections and the discrete cues. The effect of 0.015 mg/kg of 3pMBP on vehicle priming were also tested in order to determine whether 3pMBP per se would affect responding after extinction.

Results

3pMBP inhibits ($ID_{50}\approx 0.005$ and $ID_{100}\approx 0.015$ mg/kg) the intravenous self-administration of THC in non-human primates (Squirrel Monkeys) (FIGS. 7A and 7B). 3pMBP also inhibited ($ID_{100}\leq 0.0015$ mg/kg) the reinstatement of THC-seeking in non-human primates (Squirrel Monkeys) induced by THC priming but had no effect on vehicle priming (FIGS. 7C and 7D).

Conclusion

The results of the experiments to evaluate the effects of 3pMBP on the conditioned and unconditioned effects of THC are reported in the table hereinafter (Table 3). This table clearly shows that 3pMBP is very potent in inhibiting a large spectrum of THC effects related to several disorders that appear after cannabinoids use. Consequently, 3pMBP appears as a general treatment of Cannabinoids-Related Disorders.

body weight in a diet-induced obese (DIO) mouse model and to compare these effects to those of the CB1 orthosteric antagonist rimonabant. Body weight and food intake were studied because they are reduced by the repeated treatment with CB1 orthosteric antagonists both in mice and in humans (Wiley et al., 2005; Mazier et al., 2015; Bermudez-Silva F J, et al., 2012). DIO mice were used because the effects of CB1 antagonist are of greater amplitude in obese mice than in lean mice.

Methods and Materials

Male C57BL/6J mice were fed ad libitum with a high-fat diet (HFD) for 8 weeks before the start of the pharmacological treatments. During pharmacological treatments, the HFD was maintained and food intake and body weight were measured daily. The food consumed was calculated by subtracting the food left in the hoppers from the initial pre-weighted amount. In a first experiment (n=10-7 per

TABLE 3

Summary of the preclinical evaluation of 3pMBP as a treatment of Cannabinoids-Related Disorders

| | Test system | ID50 (mg/kg) | ID100 (mg/kg) | % inhibition |
|---|---|---|---|---|
| Unconditioned effects of THC | | | | |
| THC-induced increase in food intake | mice | 0.015 | 0.05 | 100 |
| THC-induced increase in psychomotor stimulation | mice | 0.00036 | 0.0015 | 100 |
| THC-induced impairment of pre-pulse inhibition | mice | 0.0045 | 0.015 | 100 |
| THC-induce impairment of working memory | mice | ND | 0.15 | 100 |
| THC-induce impairment of long-term memory | mice | <0.005 | ND | 100 |
| THC-induced impairment of social interaction | mice | 0.005 | 0.015 | 100 |
| THC-induced impairment of reality testing | mice | <0.015 | ND | 100 |
| THC-induced catalepsy | mice | 0.005 | 0.05 | 50 |
| THC-induced gaping behavior | rats | <0.005 | ND | 50 |
| THC-induced impairment of dopamine release | rats | 0.005 | 0.015 | 50 |
| Conditioned effects of THC & WIN 55,212-2 | | | | |
| Intravenous self-administration of the CB1 agonist WIN 55,212-2 | mice | 0.005 | 0.015 | 80 |
| Intravenous self-administration of THC | monkeys | 0.005 | 0.015 | 80 |
| Reinstatement of THC-seeking | monkeys | <0.0015 | ND | 80 |

ND = Not Determined

Example 4: 3pMBP has None of the Behavioural and Endocrinological Side Effects of Orthosteric CB1 Antagonists The pharmacological profile and the effects on phenotypes related to adverse effects of 3pMBP and the orthosteric CB1 antagonist rimonabant were compared. Orthosteric CB1 antagonists such as Acomplia® were withdrawn from the market because of adverse effects. Consequently, for a therapeutic tool inhibiting the CB1 to be of practical use in humans it should not have the known adverse effects of orthosteric CB1 antagonists.

Known adverse effects of orthosteric antagonists of the CB1 receptors and in particular of rimonabant are: 1. A reduction of food intake and body weight that is a sign of a non-specific effect on reward pathways; 2. A induction of anxiety- and depression-related behaviours; 3. An increase in glucocorticoid secretion inducing an impairment of the subject hormonal status; 4. An induction of precipitated withdrawal in cannabinoids dependent subjects.

The inventors then analysed the effects of 3pMBP on all these parameters.

1. Effects of a Repeated Treatment with 3pMBP on Food Intake and Body Weight

These experiments aimed to evaluate the ability of a repeated treatment with 3pMBP to decrease food intake and body weight in a diet-induced obese (DIO) mouse model group) the effect of 3pMBP (0, 0.005, 0.015 and 0.05 mg/kg; in 2 ml/kg of corn oil) for four weeks were analyzed. In a second experiment (n=8 per group) the effects of 3pMBP (0, 5 and 15 mg/kg in 5 ml/kg of corn oil) were compared to those of rimonabant (10 mg/kg in 5 ml/kg of corn oil) over two weeks of treatment. 3pMBP and rimonabant were administered by oral gavage once a day, two hours before the start of the dark phase of the light/dark cycle.

Results

3pMBP at none of the dose tested did modify food intake or body weight for the whole experiment duration (four weeks for 0.005, 0.015 and 0.05 mg/kg and two weeks for 5 and 15 mg/kg). In contrast the CB1 antagonist rimonabant decreased both food intake and body weight (FIGS. 8A and 8B).

2. Effects of 3pMBP on Precipitated Withdrawal

These experiments aimed to evaluate the ability of 3pMBP to precipitate withdrawal in mice chronically treated with THC. Precipitated withdrawal was studied because it could constitute a potential side effect of a THC inhibitor in cannabinoids dependent subjects. For example, the orthosteric CB1 antagonist rimonabant is known to precipitate withdrawal in mice chronically treated with TIC.

Materials and Methods

The chronic THC regimen (20 mg/kg, twice a day) used in these experiments has been chosen because it mimics heavy marijuana use (Cook et al., 1998) and is considered as a model of cannabinoids dependence in mice (Cutando et al., 2013; Hutcheson et al., 1998). The effects of rimonabant (10 mg/kg) and of 3pMBP (0.15 mg/kg) were studied in independent experiments in CD1-Swiss mice. From day 1 to 4-5, mice were injected ip with vehicle or THC (20 mg/kg in NaCl 0.9% containing 2% ethanol and 2% Tween80, 10 ml/kg) twice a day. On the last day of treatment, mice in the THC group received the administration of rimonabant or 3pMBP. All the other animals received the administration of the respective vehicle. Recordings were analyzed for 45 min immediately (rimonabant) or 3 h (3pMBP) after administration. The dose and schedule of administration of rimonabant chosen for this study has been commonly used to precipitate THC withdrawal in mice (Cook et al. 1998, Hutcheson et al., 1998, Huang et al., 2009).

For the measure of precipitated withdrawal, mice were placed in a novel home cage and a video camera positioned in front of each cage recorded animals' behaviors. Scoring was performed for 1 minute every 5 min-period. Two withdrawal signs were analyzed: paw tremors and head shaking, since they are the most common signs of THC withdrawal observed in mice (Cook et al. 1998, Hutcheson et al., 1998, Lichtman et al., 2001).

Results

3pMBP did not precipitate withdrawal in mice. In contrast, in the same experimental conditions, withdrawal signs appeared after administration of the CB1 orthosteric antagonist rimonabant (FIGS. 8C and 8D).

3. Effects of a Repeated Administration of 3pMBP on Anxiety- and Depression-Related Behaviors in Mice These experiments aimed to evaluate the ability of a repeated treatment with 3pMBP to increase anxiety and depression related behaviors in mice and to compare these potential effects with those of the orthosteric CB1 antagonist rimonabant. Anxiety- and depression-related behaviors were studied because an increase in anxiety and depression are consequences of repeated treatment with CB1 orthosteric antagonists both in rodents and in humans (Bellocchio et al., 2013, Patel et al., 2006, Moreira et al., 2009, Tzavara et al., 2003). Anxiety-like behaviors were studied in the elevated plus maze (EPM) because this model is widely used in rodents to evaluate the putative anxiogenic or anxiolytic effects of pharmacological compounds (Walf et al., 2007). Depression-related behaviors were studied using the sucrose preference test that is largely used as a model of anhedonia, one of the cardinal symptoms of depression.

Material and Methods

The EPM apparatus was made of four elevated arms arranged in a cross-like disposition, with two opposite arms being enclosed by walls and the two other arms being open. For all the experiments, after receiving the appropriate treatment mice were placed in the center of the EPM and let free to explore the maze for 5 minutes. The time spent and the number of entries into the open arms and closed arms were measured by an automatic videotracking system. A decrease in the percentages of visits and/or of the time spent in open arms is considered an index of increase in anxiety levels.

The sucrose preference test was performed in the home cage of the mice. Two identical bottles, one containing water and the other one containing a 2%-sucrose solution were placed in the hopper of each home cage. The mice had an unlimited access to water and sucrose solutions during the activity phase, the dark phase of the light/dark cycle that started at 7 pm. The volumes of water and of sucrose solutions drank by the mice were measured over two 1.30 h intervals, the first between 7.00 pm and 8.30 pm and the second between 8.30 pm and 10.00 pm. At each time point, the bottles were weighed and the intake volume was calculated by subtracting the initial bottle weight to the final bottle weight.

Male C57BL/6J mice (n=6-8 per group) received either one daily administration of 3pMBP (0.05; 5 or 15 mg/kg), rimonabant (10 mg/kg) or of the respective vehicles for 28 days. At day 26, mice were subjected to the EPM and at day 28 to the sucrose preference test. All the behavioral procedures started 3 hours after 3pMBP or vehicle of 3pMBP (0 mg/kg) treatment and 30 min after rimonabant or vehicle of rimonabant (0 mg/kg) treatment.

Results

3pMBP had no effects on anxiety and depression related behaviors as measured in the EPM (FIGS. 9A and 9B) and sucrose preference test (FIG. 9C) respectively. In contrast rimonabant increased anxiety and depression-related behavior as shown by the decrease of the time spent in the open arms of the EPM (FIG. 9A) and on the percentage of visits in the open arms (FIG. 9B) and the decrease in the preference for sucrose (FIG. 9D).

4. Effects of 3pMBP on Glucocorticoid Secretion in Mice

These experiments aimed to evaluate in mice the effects of 3pMBP on plasma concentrations of corticosterone, the main glucocorticoid produced by the adrenal gland in rodents corresponding to cortisol in humans. The effects of 3pMBP on corticosterone levels were studied because the orthosteric CB1 antagonist rimonabant increase plasma corticosterone concentrations (Steiner et al., 2008).

Materials and Methods

The effects of 3pMBP (0.3 and 10 mg/kg) or vehicle (VEH) on plasma corticosterone levels were studied in male and female CD-1 Swiss mice. Blood sampling was performed 2, 5, 8 and 24 h after dosing (n=3 per gender, per dose and per sampling time). For blood sampling mice were anaesthetized under isoflurane and blood was collected by cardiac puncture. Blood was centrifuged, plasma was taken and frozen at −80° C. until quantifications of corticosterone by GC-MS/MS (gas chromatography-tandem mass spectrometry) using a validated GC-MS method described elsewhere (Vallée et al., 2014; Vallée et al., 2000; George et al., 2010).

Results

3pMBP at 0.3 and 10 mg/kg did not increase glucocorticoid secretion in male (FIG. 10A) and in female (FIG. 10B) mice.

Conclusion

The adverse effect of rimonabant are compared with the effects of 3pMBP in Table 4.

TABLE 4

3pMBP has none of the adverse effects of rimonabant

| IN VIVO | TEST SYSTEM | 3pMBP | | | Rimonabant | | |
|---|---|---|---|---|---|---|---|
| | | Effect | Highest dose tested (mg/kg) | N fold IC50* | Effect | IC100 (mg/kg) | N fold IC100** |
| Inhibition of food-intake and body weight (repeated administration) | male mice | No | 15 | 3000 | Yes | 10 | 1 |
| Precipitated withdrawal in THC dependent mice | male mice | No | 0.15 | 30 | Yes | 10 | 1 |
| Increase in anxiety and depression related behaviors (repeated administration) | male mice | No | 15 | 3000 | Yes | 10 | 1 |
| Increase in glucocorticoid secretion | male + female mice | No | 10 | 2000 | Yes | 2 | 0.2# |

*0.005 mg/kg most observed ID50 of 3pMBP to inhibit THC behavioral effects;
**Reference ID100 for rimonabant effects = 10 mg/kg.
from Steiner et al., 2008

The effects of 3pMBP are very different from the ones of the CB1 orthosteric antagonist rimonabant.

3pMBP has none of the typical adverse effects of rimonabant and other CB1 orthosteric antagonists, such as decrease in food intake, increase in anxiety- and depression-related behaviours, precipitated withdrawal in THC dependent animals and increase in glucocorticoid secretion.

This lack of effects of 3pMBP was observed for all the highest doses used in each test. These doses were several times higher (in mg/kg) than the ID50 (0.005 mg/kg) of 3pMBP to inhibit the self-administration of CB1 agonists and THC, respectively: 30 times higher for precipitated withdrawal; 2000 times higher for glucocorticoid secretion; and 3000 times higher for food intake, body weight, anxiety and depression related behaviours.

Example 5: 3pMBP has No Effect on Spontaneous Behaviour in Mice

In addition to not having the same adverse behavioural effects of orthosteric CB1 antagonists 3pMBP had no detectable effects on behaviour per se in rodents as shown by the video analysis of spontaneous behaviour in the home cage during 24 hours after the administration of 3pMBP in mice at 15 mg/kg.

Example 6: 3pMBP has No Effect on Mood and Cognitive Performance in Humans

These experiments were designed to evaluate the effects of single and repeated ascending doses of 3pMBP on mood, cognition and suicidality in humans using a battery of validated tests.

Material and Methods

Two studies were performed. In the first study independent cohorts of healthy volunteers received a single administration of 3pMBP at one of the 3 escalating doses (0.2, 0.6; 2 mg/subject) or placebo. In each dose cohort, using a double-blind procedure, 6 subjects received the assigned dose of 3pMBP and 2 subjects received placebo. In the second study, independent cohorts of healthy volunteers received repeated administrations of 0.6 mg/subject of 3pMBP (once a day for 7 days). In each dose cohort, using a double-blind procedure, 6 subjects received the assigned dose of 3pMBP and 2 subjects received placebo. The 0.2 mg/subject dose induces an increase in plasma concentrations of 3pMBP that are in the range of the ones observed at the most observed ED100 (0.015 mg/kg) for inhibition of THC behavioral effects in rodents.

In both studies, after 3pMBP dosing subjects were also submitted to a general observation of their behaviour by a certified clinician and the following tests were performed.

Bond & Lader VAS

Bond and Lader Visual Analogue Scale (Bond and Lader, 1974) consists of 16 bipolar self-rating 100-mm long lines between two opposite adjectives. The test is computer-assisted. The subject has to indicate on each line how he is feeling at the time of the test, using the mouse. The response is scored by measuring the distance in mm between the left end of the line and the subject's mark. The score consists of three derived factor sub-scores: alertness, contentedness (well-being) and calmness. A higher score indicates a higher alertness, contentedness and calmness.

ARCI 49

This self-administered and computer-assisted questionnaire consists of 49 items. Each question appears one by one on the screen. Using the mouse, the subject must click on "false" or "true" to each item, in regard to what he is feeling at the time he is reading it. Then 5 scores are derived: PCAG (Pentobarbital Chlorpromazine Alcohol Group Scale), BG (Benzedrine group), AG (Amphetamine Group Scale), LSD (LSD Group Scale) and MBG (Morphine Benzedrine Group Scale) (Martin et al., 1971).

POMS 65

The Profile Mood Scale consists of 65 adjectives describing various mood feelings (Mc Nair et al., 1992; Cayrou et al., 2000; Cayrou et al., 2003).

This version is a computerized version. Each adjective appear one by one on the screen and the subject is asked to describe how these adjectives reflect his mood at the time he is completing the questionnaire, rating each description on a 5 points scale of increasing agreement: from "not at all" to "extremely".

Six scores are classically derived from the questionnaire: tension-anxiety (TA); depression-dejection (DD); anger-hostility (AH); vigor-activity (VA); fatigue-inertia (FI); confusion-bewilderment (CB).

Columbia Suicide Severity Rating Scale (C-SSRS)

The relationship between medications entering the CNS and the potential for suicidality (suicidal ideation and behavior) has recently received heightened attention by regulatory agencies, such as FDA, and raised the need to proactively implement more consistent and stringent mechanisms of data collection in clinical trials.

The prospective assessment of suicidality is collected using the Columbia-Suicide Severity Rating Scale (C-SSRS). The C-SSRS is designed to assess both suicidal behavior and suicidal ideation and consists of two questionnaires: one designed for the baseline assessment (covers the subject's lifespan until the baseline visit) and one used during the study ("Since last visit" questionnaire).

Results

For all 3pMBP doses tested there was no modification in the general behavior of the subject and no modification for any of the psychometric tests performed. In particular, no modifications in the ARCI-49 test indicate that the subjects are unable to tell that they have received a psychoactive substance.

In conclusion the data show that in humans, as observed in animals, administration of 3pMBP does not significantly modify basal behavior, mood and cognitive performance.

Example 7: Safety Pharmacology and Toxicology of 3pMBP Comparison with Rimonabant 1. GLP Safety Pharmacology Evaluation of 3pMBP
Materials and Methods Evaluation of the Effects of 3pMBP on hERG Current in Stably Transfected HEK-293 Cells:

The aim of this study was to assess any possible effects of 3pMBP on hERG tail current in stably transfected HEK-293 cells. The study was carried out following general requirements of GLP and the study design follows ICH S7A guidelines (2001) for Safety Pharmacology. 3pMBP was studied in 3 HEK-293 cells stably transfected with hERG. On each cell, the following treatments were tested: Tyrode; Vehicle of 3pMBP (0.3% DMSO in Tyrode) and 3pMBP at $10.98 \times 10^{-8}$ M, $10.98 \times 10^{-7}$ M and 3pMBP at $10.98 \times 10^{-6}$ M.

E-4031 was used as positive control and was tested in one separate HEK-293 cell to support the validity of the method used.

Cells were clamped to −80 mV, depolarised to 0 mV for 5 sec allowing activation of hERG current and repolarised to −50 mV for 5 sec allowing hERG tail current to deactivate. This experimental procedure was repeated at a frequency of 0.06 Hz. Currents were filtered at 1 kHz and acquired at the frequency of 2 kHz. Amplitude of hERG tail current was measured during the repolarizing pulse from 0 to −50 mV. Cells were perfused with Tyrode solution and subsequently with Tyrode solution containing 3pMBP for at least 5 minutes until steady state was reached for each perfusion period. Currents were measured before and after exposure to the test item.

Effect of 3pMBP on the Irwin Tests and Body Temperature in Rats:

The aim of this study was to assess any potential neurobehavioral effects and effects on body temperature of 3pMBP following single oral administration in the rat.

The study was carried out following general requirements of GLP and the study design follows the ICH S7A guideline (2001) for Safety Pharmacology.

The study involved 4 groups of 6 male Wistar rats weighing between 154.0 and 185.9 g. Groups were dosed respectively with vehicle (corn oil, i.e. control group), or with 3pMBP at 2, 9 or 36 mg/kg.

On study day, animals were firstly scored by the Irwin standardized observation battery and the body temperature was measured. Subsequently, they were dosed by the oral route with one of the 3pMBP doses or its vehicle in a volume of 4 ml/kg. Then the Irwin scores as well as measurement of body temperature were performed again at 1, 3, 6, 8 and 24 hours after the administration.

Evaluation of Effect of 3pMBP on Respiration in the Unrestrained Conscious Rat Following Single Oral Administration The aim of this study was to assess any possible effect of a single oral administration of 3pMBP on respiratory parameters (respiratory rate, peak inspiratory and peak expiratory flows, inspiration and expiration times, airway resistance index, tidal volume and minute volume) measured by the whole body plethysmography method in conscious rats.

The study was carried out following general requirements of GLP and the study design follows the ICH S7A guideline (2001) for Safety Pharmacology.

The study involved 4 groups of 6 male Wistar rats, groups were dosed respectively with vehicle (corn oil, i.e. control group), or with 3pMBP at 2, 9 or 36 mg/kg.

The day prior to the study, animals were only allowed to drink water. On the study day, animals were placed in the plethysmograph and measurements started immediately afterwards. The whole body plethysmography method measure in a closed chamber variations in air flow due to thoracic cage movements during respiration and enables the measurement of respiratory parameters in the conscious animal, totally free to move about. At least 15 minutes after the start of measurements, animals were dosed with 3pMBP or its vehicle by the oral route in a volume of 4 ml/kg. Respiration was recorded for a total period of 6 hours following the dosing. Respiratory parameters were determined from analysis of respiratory cycles.

Evaluation of Effects of 3pMBP on Blood Pressure, Heart Rate, Electrocardiogram and Body Temperature after Single Oral Administration to Conscious Dogs The aim of this study was to evaluate any possible effects of 3pMBP on blood pressure, heart rate, body temperature and electrocardiogram after single oral administration to conscious dogs.

The study was carried out following general requirements of GLP and the study design follows the ICH S7A guideline (2001) for Safety Pharmacology.

The study involved 4 male Beagle which were previously instrumented with telemetry transmitters for arterial blood pressure, body temperature and electrocardiogram measurements.

The study was conducted in two parts. In part I, each animal received vehicle (i.e., corn oil), 3pMBP at 2, 9 and 36 mg/kg by the oral route according to an ascending dose design with a washout period of one week between doses. Telemetry measurements of arterial blood pressure, heart rate, body temperature and electrocardiogram (epicardial Lead II) started at least 2 hours before each dosing and continued for at least 24 hours after dosing. In part II, animals were dosed again with 3pMBP either at 9 or at 36 mg/kg (n=2 per dose level) by the oral route for complementary investigations, i.e., blood sampling and observation of animals.

Results

3pMBP did not show any adverse effects on the GLP safety pharmacology tests:

1. In vitro, 3pMBP (100 nM, 1 μM and 10 μM) did not modify hERG (human ether-ago-go-related gene) tail currents in HEK-293 cells stably transfected with hERG-1 cDNA.

2. In vivo, 3pMBP (2, 9 and 36 mg/kg) did not modify: a. Behavior (Irwin test) and body temperature in rats; b. respiration in conscious rats; and c. blood pressure, heart rate, electrocardiogram and body temperature in conscious dogs.

The only effect reported was a decrease in heart rate high frequency rhythms and oscillations associated with a decrease in heart rate variability at the dose of 9 mg/kg only in the dog. This finding suggests an effect on autonomic balance and, more precisely, a decrease in vagal activity. However, this effect was mild since it did not cause any change in heart rate and cannot be considered as an adverse effect by itself.

2. GLP Toxicology Evaluation of 3pMBP

Materials and Methods

Cytotoxic, mutagenic and genotoxic effects of 3pMBP have been tested up to the maximal concentrations acceptable for the test systems, i.e. between 74 and 100 μM.

These doses are approximately 7 400 and 10 000 higher than the highest IC50 of 3pMBP (10 nM) to inhibit CB1-mediated cellular effects of THC.

The toxicology studies in vitro performed to characterize 3pMBP were: 1. The AMES test+/−metabolic activation (GLP); 2. The human Chromosome Aberration test+/−metabolic activation (GLP); 3. Cytotoxicity on primary culture of neuron and hepatocytes (non-GLP). Repeated dose toxicity studies were performed in rats and dogs. These two species were selected because both species express the CB1 receptor and have been classically and successfully utilized to identify the toxic effects of CB1 orthosteric antagonists, such as rimonabant. In addition, the putative pregnenolone binding site has 100% homology in rats, dogs and humans. Finally, protein binding studies suggest that the binding of 3pMBP did not differ between rats (84-94%), dogs (84-105%), and humans (88-98%), whilst it seemed higher in monkeys (97-99%).

The repeated toxicology studies performed to characterize 3pMBP were 28-day oral toxicity studies (GLP) in rats and dogs with three doses (2 mg/kg, 9 mg/kg and 36 mg/kg).

Results

In Vitro Studies

3pMBP did not show any cytotoxicity, genotoxicity and mutagenesis even at the highest concentration tested (between 74 and 100 μM). Concentrations of 74 and 100 μM of 3pMBP are 7 400-10 000 times higher than the IC50 of 3pMBP for inhibiting CB1-dependent MAPK phosphorylation.

In Vivo Studies

TABLE 5

Summary of the in vivo toxicity studies with 3pMBP in rats and dogs

| | Multiple doses oral toxicology | | | |
|---|---|---|---|---|
| Days of treatment | 28 | 28 | 28 | 28 (+14) |
| 3pMBP Dose (mg/kg) | 2 | 9 | 36 | 36 |
| Vehicle Corn oil (ml/kg) | 4 | 4 | 4 | 4 |
| Number of rats | 10M, 10F | 10M, 10F | 10M, 10F | 10M, 10F |
| Number of dogs | 3M, 3F | 3M, 3F | 3M, 3F | 2M, 2F |
| Mortality | NOE | NOE | NOE | NOE |
| Clinical signs | NOE | NOE | NOE | NOE |
| Body temperature | NOE | NOE | NOE | NOE |
| Body weight | NOE | NOE | NOE | NOE |
| Food consumption | NOE | NOE | NOE | NOE |
| Ophthalmology | NOE | NOE | NOE | NOE |
| Cardiovascular parameters | $NA_R$, $NOE_D$ | $NA_R$, $NOE_D$ | $NA_R$, $NOE_D$ | NA |
| Haematology & coagulation | NOE | NOE | NOE | NOE |
| Blood chemistry | $NOAE_R$, $NOE_D$ | $NOAE_R$, $NOE_D$ | $NOAE_R$, $NOE_D$ | $NOAE_R$, $NOE_D$ |
| Urinalysis | $NOAE_R$, $NOE_D$ | $NOAE_R$, $NOE_D$ | $NOAE_R$, $NOE_D$ | $NOAE_R$, $NOE_D$ |
| Organ weight | $NOAE_R$, $NOE_D$ | $NOAE_R$, $NOE_D$ | $NOAE_R$, $NOE_D$ | $NOAE_R$, $NOE_D$ |
| Macroscopic findings | NOE | NOE | NOE | NOE |
| Histopathology | NOE | NOE | NOE | NOE |

M = males; F = females; NOE = non observed effects; NOAE = non observed adverse effects; NA = not analyzed; if not specified the effects were observed in both rats and dogs. $NOAE_R$ and $NOE_R$ = change observed only in the rat; $NOAE_D$ and $NOE_D$ = change observed only in the dog.

In vivo, 3pMBP has in the rat a NOAEL (Non observed adverse effect level) >36 mg/kg/day/28 days and in the dog a NOEL (Non observed effect level) >36 mg/kg/day/28 days.

Considering that the most observed ID50 of 3pMBP for inhibiting the effects of THC in mice, rats and non-human primates is 0.005 mg/kg, 3pMBP has a therapeutic index (TI) >7200.

Conclusion

Based on the results of the toxicology experiments, 3pMBP shows a favorable toxicity profile with a TI >7200. Such a large TI could be the result of two characteristics of 3pMBP:

1. A unique and very selective mechanism of action (MoA) not found in other approved drugs and, per our knowledge, not yet tested in other preclinical developments. Thus, 3pMBP seems to solely inhibit the activity of one of the THC-induced signaling pathways (MAPK) and has no effect on THC independent, CB1-mediated phenotypes in vivo.

2. A low conversion to drug-derived metabolites that are very often are responsible for the in vivo toxicity of NCEs.

As shown in FIG. 12, the safety and toxicity profile of 3pMBP was very different from the one of the orthosteric CB1 antagonist rimonabant. Thus rimonabant induced several adverse events at doses quite close to the therapeutic dose and in particular clonic convulsion, hepatotoxicity and several profound alterations in behavior.

Example 8: Pharmacokinetics, Adsorption, Distribution, Metabolism and Excretion Studies of 3pMBP

1. Pharmacokinetics and Absorption of 3pMBP in Animals

Materials and Methods

The pharmacokinetics (PK) of 3pMBP in plasma was studied in male and female mice rats and dogs after per os administration (in corn oil) by gavage. Distribution of 3pMBP in the brain was studied in mice and rats. In dogs, 3pMBP was also administered intravenously after solubilisation in cyclodextrine. Both in plasma and brain, concentrations of 3pMBP were measured using liquid chromatography coupled to a tandem mass spectrometry (LC/MS-MS).

Results

There was no difference between males and females in the PK parameters of 3pMBP in the plasma after administration to mice (0.3, 4 and 10 mg/kg, per os) rats (1.6 mg/kg, per os) and dogs (0.7 mg/kg, per os and iv). As described in Table 6 (results from male and female animals are cumulated), the increase in AUC in plasma after single administration of 3pMBP was linear over the three doses studied in mice (0.3, 4 and 10 mg/kg). In mice, rats and dogs, the $t_{max}$ of 3pMBP was similar (≈3 h) suggesting comparable rate of absorption of 3pMBP. The half-life of 3pMBP was the longest in dogs (28.0 h per os; 35.9 iv), followed by mice (17.8-18.3 h) and was shortest in rats (8-13.9 h). AUC/dose ratios after per os administration were higher in dogs (2074), followed by mice (848-1132); the lowest was in rats (661).

In mice and rats, 3pMBP had a longer $t_{max}$ (7 h vs≈3 h) and higher AUC and $C_{max}$ in the brain than in the plasma. AUC and $C_{max}$ brain/plasma ratio seemed inversely related to the dose, with the highest ratios ($C_{max}$=2.8 and AUC=7.38) observed for 0.3 mg/kg 3pMBP in mice. The half-life of 3pMBP in the brain and plasma were similar.

Following oral or intravenous administration of 3pMBP, mice, rats and dogs showed a bi-phasic elimination profile, a rapid decrease (distribution phase) followed by a much more gradual decline up to the last sampling time (elimination phase).

In dogs, the bioavailability of 3pMBP was approximately 68%.

2. Pharmacokinetics of 3pMBP in Humans

Material and Methods

In this study independent cohorts of healthy volunteers received a single administration of 3pMBP at one of 3 escalating doses (0.2, 0.6; 2 mg/subject) or placebo. In each dose cohort using a double blind procedure 6 subjects received the assigned dose of 3pMBP and 2 subjects received placebo.

Plasma concentrations of 3pMBP were evaluated performing a full pharmacokinetic during the first 24 h hours after dosing and every 24 h thereafter.

Results

Oral administration of 3pMBP induced plasma concentration of the drug that were in the range of the ones predicted by PK studies in animals using body surface ratio conversion confirming a good absorption of 3pMBP in humans. The 0.2 mg/subject dose induced an increase in plasma concentrations of 3pMBP that are in the range of the ones observed at the most observed ED100 (0.015 mg/kg) for inhibition of THC behavioral effects in rodents.

3. Metabolism of 3pMBP

Materials and Methods

Metabolic Stability of 3pMBP in Human, Rat, Mouse and Dog Liver Microsomes:

The investigation was performed on liver microsomes (LM) coming from mouse (MLM), rat (RLM), dog (DLM) and human (HLM).

3pMBP was incubated with liver microsome pools supplemented with NADPH as cofactor. Samples were taken at 5 different times (0, 10, 20, 30 and 60 minutes) and samples were monitored for parent compound disappearance in MRM mode using LC/MS-MS. The Intrinsic Clearance and half-life have been determined. Verapamil was used as reference compound.

Metabolic Profiling of [3H]-3pMBP in Plasma and Excreta in the Rat

The metabolic profile was evaluated in plasma, in urines and feces and the radio-labelled metabolites were identified by their retention time using Radio-HPLC analysis. The results are expressed as % of the sum of all the detected peak areas.

Conversion of 3pMBP in Downstream Steroids in Mice, Rats, Dogs and Humans:

Conversion of 3pMBP in downstream steroids was studied in mice, by measuring pregnenolone downstream steroids progesterone and 17α,OH pregnenolone, that are the first two steps of pregnenolone metabolism. Conversion of 3pMBP in downstream steroids was also studied in rats and dogs after administration of 2, 9 and 36 mg/kg of the compound by measuring testosterone, DHEA and allopregnanolone. Finally, conversion in downstream steroids (DHEA, allopregnanolone and testosterone) was studied in humans after the acute administration of one of three doses (0.2, 0.6, and 2 mg/subject) of 3pMBP. In all these studies

TABLE 6

Summarized mean pharmacokinetic parameters in plasma of mice, rats and dogs after single 3pMBP administration

| Species | Dosing | Dose mg/kg | n | $C_{max}$ (ng/ml) | $T_{max}$ (h) | $AUC_{last}$ (ng/ml*h) | AUC/ dose ratio | AUC M/F Ratio | $T_{1/2}$ (h) |
|---|---|---|---|---|---|---|---|---|---|
| Mice | Per os | 0.3 | 6 | 35.5 | 2.5 | 254 | 848 | 1.1 | 17.8 |
|  |  | 4 | 6 | 490 | 2.25 | 3744 | 936 | 1.5 | 18.3 |
|  |  | 10 | 6 | 1787 | 2.25 | 11322 | 1132 | 0.9 | 18.2 |
| Rats |  | 1.6 | 9 | 116.4 | 4.1 | 1058.7 | 661.7 | 0.7 | 13.9 |
| Dogs | iv | 0.7 | 6 | 505 | 0.125 | 2192 | 3131 | 1.28 | 35.9* |
|  | per os | 0.7 | 6 | 137.7 | 2.67 | 1452.5 | 2074.5 | 0.93 | 28.0* |

Data from males and females were collapsed. The Cmax and AUC values in bold should be roughly multiplied by 4 to compensate for the lower dose actually administered.
*t½ determined using a manual linear regression technique choosing the last three points of each PK curve.

plasma concentrations of steroids were measured by gas chromatography-tandem mass spectrometry (GC/MS-MS).

Results

Metabolic Stability in Liver Microsomes (LM)

3pMBP had a low clearance in human and rat LM (intrinsic clearance=3.38 and 12.3 μl/min/mg; half-life=410 and 113 min, respectively) and a moderate clearance in dog and mice LM (intrinsic clearance=26.0 and 29.7 μl/min/mg and half-life=53.4 and 46.6 min, respectively).

Metabolic Profile in the Rat

In vivo, [$^3$H]-3pMBP does not produce any major metabolites in plasma. The compound is excreted prevalently through the feces where most of the metabolism seems to occur. In the plasma at three and six hours post oral administration of [$^3$H]3pMBP, only one major peak, corresponding to 3pMBP, was observed accounting for respectively 100% (3 h) and 78% (6 h) of all integrated peaks. At 24 hours, 3pMBP was not present in the plasma and there were only traces of one metabolite. In the urine, there was little 3pMBP detected (less than a 0.5% dose) at each time interval. At the 0-6-hour interval, three major peaks were detected (≈30% each) including the one corresponding to 3pMBP. At 6-24 h and 24-48 h no 3pMBP was detected in the urine and only the two other peaks were present. Most of the dose excreted was found in the feces in which, in addition to 3pMBP, seven other peaks were found accounting each between 30 and 10% of the integrated peaks.

Conversion of 3pMBP in Downstream Steroids

The administration of 3pMBP at 0.3 and 10 mg/kg per os did not increase the plasma concentrations of progesterone and 17-OH-pregnenolone, the first two steps of pregnenolone metabolism, measured in male and female mice 2, 5, 8 or 24 hours after 3pMBP administration. Similarly, in male and female rats and dogs there was no effect of acute or repeated (28 days) administration of 3pMBP (2, 9, and 36 mg/kg) on plasma concentrations of testosterone, DHEA and, allopregnanolone, measured at predose and then 1 h, 2 h, 4 h, 8 h and 24 h post-dose. Finally, no changes in active steroids were observed in humans for all the doses of 3pMBP tested.

4. Interaction of 3pMBP with Metabolic Enzyme CYP, UGT and Cellular Transporters Material and Methods The potential inhibition by 3pMBP of the activity of several CYP isozymes (1A, 2B6, 2C8, 2C9, 2C19, 2D6, 3A) was tested in vitro using human liver microsomes.

3pMBP was pre-incubated at a single concentration (10 μM) with substrate and pooled human liver microsomes. Reaction was initiated by adding NADPH-generating compounds and after stopping of reaction and samples treatment; HPLC-UV/VIS and HPLC-MS/MS detection were used for detection of peak areas corresponding to the metabolite of each substrate.

3pMBP (10 μM) was tested in the UGT1A1 inhibition (recombinant, scopoletin substrate) assay. 3pMBP is pre-incubated with UGT1A1 and the fluorescent substrate scopoletin in Tris buffer (pH 7.5) for 15 minutes at 37° C. The reaction is initiated by adding the co-factor uridine-diphosphoglucuronic acid (UDPGA), the incubation is continued for 60 minutes and relative fluorescence intensity (RFI) is measured on a fluorescent plate reader.

The potential of test compound 3pMBP to induce CYP1A2, CYP2B6 and CYP3A4 was tested in vitro in triplicates at test concentrations of 0.01, 0.1, and 1 μM using mRNA level as the end point.

The inhibition by 3pMBP of the activity of different cellular transporters (OCT2, BCRP, OAT1, OAT3, OATP1B1, OATP1B3, P-gp) was tested in vitro.

The effects of 3pMBP (10 μM), and of reference inhibitors of each transporter, were studied in cell line over expressing the target cellular transporters. Chinese Hamster Ovary (CHO) were used for all transporters except for P-gp that was studied in Madin-Darby Canine Kidney (MDR1-MDCKII) cells. The inhibition of the activity of each transporter is evaluated by measuring changes in the transport of their specific substrates by fluorometry.

Results

3pMBP at 10 μM induced no significant inhibition of the activity of CYP isozymes (1A, 2B6, 2C8, 2C9, 2C19, 2D6, 3A) and at 10 nM, 100 nM and 1 μM did not increase the expression of CYP1A2, CYP2B6 and CYP3A4.

Following FDA guidance, 3pMBP could be labelled as a drug non-interacting with CYP enzymes.

In addition, 3pMBP (10 μM) did not modify the activity of UGT1A1 and of several cellular transporters (OCT2, BCRP, OAT1, OAT3, OATP1B1, OATP1B3, P-gp).

Conclusion

Overall 3pMBP shows favorable Adsorption/Distribution/Metabolism/Excretion characteristics that do not differ between males and females and that are similar between mice, rats, dogs, and humans with the exception of a longer half-life and a higher AUC in dogs and in humans than in the other two species. 3pMBP also has a good bioavailability (68% in dogs).

3pMBP shows a four times higher AUC in the brain than in the plasma.

3pMBP is also metabolically stable. It is not converted into downstream steroids in mice, rats and dogs and humans. It shows the highest in vitro stability in liver microsomes and hepatocytes in humans when compared to other species. In the rat, in vivo, 3pMBP does not produce any metabolite above trace levels in the plasma and most of the compound is excreted as such trough the feces.

Finally, 3pMBP does not inhibit the activity of major human CYP, UGT isoenzymes and cellular transporters, nor does it induce the expression of CYP isoenzymes.

Adams A J, Banister S D, Irizarry L, Trecki J, Schwartz M, Gerona R, "Zombie" Outbreak Caused by the Synthetic Cannabinoid AMB-FUBINACA in New York. N Engl J Med. 2017 Jan. 19; 376(3):235-242

Bellocchio L, Lafenêtre P, Cannich A, Cota D, Puente N, Grandes P et al. Bimodal control of stimulated food intake by the endocannabinoid system. NatNeurosci 2010. 13, 281-283.

Bellocchio L, Soria-Gómez E, Quarta C, Metna-Laurent M, Cardinal P, Binder E, et al. Activation of the sympathetic nervous system mediates hypophagic and anxiety-like effects of $CB_1$ receptor blockade. Proc Natl Acad Sci USA. 2013 Mar. 19; 110(12):4786-91.

Bermudez-Silva F J, Cardinal P, Cota D. The role of the endocannabinoid system in the neuroendocrine regulation of energy balance. J Psychopharmacol. 2012 January; 26(1):114-24.

Bond and Lader, Br. J. Med. Psychol. 1974; 47: 211-218

Busquets-Garcia A, Soria-Gómez E, Redon B, Mackenbach Y, Vallée M, Chaouloff F, Varilh M, Ferreira G, Piazza P V, Marsicano G. Pregnenolone blocks cannabinoid-induced acute psychotic-like states in mice, 2017 November; 22(11):1594-1603

Cayrou S., Dickès P. & Dolbeault S. Profile Of Mood States (POMS-f) Journal de Thérapie Comportementale et Cognitive, 2003, 13(2), 83-88.

Cayrou S., Dickés P., Gauvain-Piquard A., Dolbeault S., Callahan S. &Roge B. Validation de la traduction française du POMS (Profile Of Mood States). Psychologie et Psychométrie, 2000, 21(4), 5-22.

Cerdá M, Wall M, Keyes K. M, Galea S, and Hasin D. Medical marijuana laws in 50 states: investigating the relationship between state legalization of medical marijuana and marijuana use, abuse and dependence. Drug Alcohol Depend. 2012; 120, 22-27;

Cook S A, Lowe J A, Martin B R. CB1 receptor antagonist precipitates withdrawal in mice exposed to Delta9-tetrahydrocannabinol. J Pharmacol Exp Ther. 1998 June; 285(3):1150-6.

Cutando L, Busquets-Garcia A, Puighermanal E, Gomis-González M, Delgado-García J M, Gruart A, Maldonado R, Ozaita A. Microglial activation underlies cerebellar deficits produced by repeated *cannabis* exposure. J Clin Invest. 2013 July; 123(7):2816-31.

D'Souza D C. Cannabinoids and psychosis. Int Rev Neurobiol. 2007 78:289-326.

DSM-V Diagnostic and Statistical Manual of Mental Disorders, 5th Edition. 2013 Washington D.C., USA: American Psychiatric Press.

Ennaceur A. One-trial object recognition in rats and mice: Methodological and theoretical issues. Behav Brain Res. 2010 Dec. 31; 215(2):244-54

Galli J. A., Sawaya R. A., Friedenberg F. K. Cannabinoid hyperemesis syndrome. Current Drug Abuse Reviews. 2011; 4(4):241-249

EPAR (EMEA) discussion: http://www.ema.europa.eu/docs/en_GB/document_library/EPAR_-_Scientific_Discussion/human/000666/WC500021284.pdf George O, Vallée M, Vitiello S, Le Moal M, Piazza P V, Mayo W. Low brain allopregnanolone levels mediate flattened circadian activity associated with memory impairments in aged rats. Biol Psychiatry. 2010 Nov. 15; 68(10):956-63

Hall W, and Degenhardt L. Adverse health effects of non-medical *cannabis* use. Lancet 2009 374, 1383-1391.

Howlett A C, Barth F, Bonner T I, Cabral G, Casellas P, Devane W A, Felder C C, Herkenham M, Mackie K, Martin B R, Mechoulam R, Pertwee R G. International Union of Pharmacology. XXVII. Classification of cannabinoid receptors. Pharmacol Rev. 2002 June; 54(2): 161-202.

Huang P, Liu-Chen L Y, Unterwald E M, Cowan A. Hyperlocomotion and paw tremors are two highly quantifiable signs of SR141716-precipitated withdrawal from delta9-tetrahydrocannabinol in C57BL/6 mice. Neurosci Lett. 2009 Nov. 6; 465(1):66-70.

Hutcheson D M, Tzavara E T, Smadja C, Valjent E, Roques B P, Hanoune J, Maldonado R. Behavioural and biochemical evidence for signs of abstinence in mice chronically treated with delta-9-tetrahydrocannabinol. Br J Pharmacol. 1998 December; 125(7):1567-77.

International Conference On Harmonisation Of Technical Requirements For Registration Of Pharmaceuticals For Human Use. The nonclinical evaluation of the potential for delayed ventricular repolarization (QT interval prolongation) by Human pharmaceuticals S7B. Revised Step.

Khan M, Pace L, Truong A, Gordon M, Moukaddam N, Catatonia secondary to synthetic cannabinoid use in two patients with no previous psychosis Am J Addict, 25 (1) (2016), pp. 25-27

Kedzior K K, Martin-Iverson M T. Chronic *cannabis* use is associated with attention-modulated reduction in prepulse inhibition of the startle reflex in healthy humans. J Psychopharmacol. 2006. 20: 471-84.

Kirkham T C. Endocannabinoids in the regulation of appetite and body weight. Behav Pharmacol 2005.16, 297-313.

Lafaye G, Karila L, Blecha L, Benyamina A, *Cannabis*, cannabinoids, and health, Dialogues Clin Neurosci. 2017 September; 19(3): 309-316.

Leggio G M, Cathala A, Neny M, Rouge-Pont F, Drago F, Piazza P V, Spampinato U. In vivo evidence that constitutive activity of serotonin2C receptors in the medial prefrontal cortex participates in the control of dopamine release in the rat nucleus accumbens: differential effects of inverse agonist versus antagonist. J Neurochem. 2009 October; 111(2):614-23

Lichtman A H, Fisher J, Martin B R. Precipitated cannabinoid withdrawal is reversed by Delta(9)-tetrahydrocannabinol or clonidine. Pharmacol Biochem Behav. 2001 May-June; 69(1-2):181-8.

Malinen H, Hyytiä P. Ethanol self-administration is regulated by CB1 receptors in the nucleus accumbens and ventral tegmental area in alcohol-preferring AA rats. Alcohol Clin Exp Res. 2008 November; 32(11):1976-83.

Martin W R, Sloan J W, Sapira J D and Jasinski D R. Physiologic, subjective, and behavioral effects of amphetamine, methamphetamine, ephedrine, phenmetrazine, and methylphenidate in man. Clin. Pharm. Ther. 1971 12: 245-258, 1971.

Mazier W, Saucisse N, Gatta-Cherifi B, Cota D. The endocannabinoid system as pivotal orchestrator of obesity and metabolic disease. Trends Endocrinol Metab. 2015 October; 26(10):524-37.

McNair D M, Lorr M, Droppleman L F. Edits manual for the profile of mood states. San-Diego, Calif.: Educational and industrial testing service, 1992.

Moreira F A, Grieb M, Lutz B. Central side-effects of therapies based on CB1 cannabinoid receptor agonists and antagonists: focus on anxiety and depression. Best Pract Res Clin Endocrinol Metab. 2009 February; 23(1):133-44.

Nagai H, Egashira N, Sano K, Ogata A, Mizuki A, Mishima K et al. Antipsychotics improve Delta9-tetrahydrocannabinol-induced impairment of the prepulse inhibition of the startle reflex in mice. Pharmacol Biochem Behav. 2006. 84: 330-6.

Patel S and Hillard C J. Pharmacological evaluation of cannabinoid receptor ligands in a mouse model of anxiety: further evidence for an anxiolytic role for endogenous cannabinoid signaling. J Pharmacol Exp Ther. 2006 July 318(1):304-11.

Petit-Demouliere B, Chenu F, Bourin M. Forced swimming test in mice: a review of antidepressant activity. Psychopharmacology (Berl). 2005 January; 177(3):245-55.

Pratt J, Winchester C, Dawson N, Morris B Advancing schizophrenia drug discovery: optimizing rodent models to bridge the translational gap. Nat Rev Drug Discov. 2012 Jun. 22; 11(7):560-79.

Rinaldi-Carmona M, Calandra B, Shire D, Bouaboula M, Oustric D, Barth F, Casellas P, Ferrara P, Le Fur G. Characterization of two cloned human CB1 cannabinoid receptor isoforms. J Pharmacol Exp Ther. 1996 August; 278(2):871-8.

S7A Safety Pharmacology Studies For Human Pharmaceuticals ICH July 2001

Sanchis-Segura C and Spanagel R. Behavioural Assessment of Drug Reinforcement and Addictive Features in Rodents: an Overview. Addict Biol 2006. 11:2-38.

Shore D M, Baillie G L, Hurst D H, Navas F, Seltzman H H, Marcu J P, et al. Allosteric modulation of a cannabinoid G protein-coupled receptor: binding site elucidation and relationship to G protein signaling. J Biol Chem. 2014 Feb. 28; 289(9):5828-45.

Steiner M A, Marsicano G, Nestler E J, Holsboer F, Lutz B, Wotjak C T. Antidepressant-like behavioral effects of impaired cannabinoid receptor type 1 signaling coincide with exaggerated corticosterone secretion in mice. Psychoneuroendocrinology. 2008 January; 33(1): 54-67.

Substance Abuse and Mental Health Services Administration (2013). Results from the 2013 National Survey on Drug Use and Health: Summary of National Findings;

Substance Abuse and Mental Health Services Administration, Center for Behavioral Health Statistics and Quality. The DAWN Report: Highlights of the 2011 Drug Abuse Warning Network (DAWN) Findings on Drug-Related Emergency Department Visits. Rockville, Md.: 2013. Feb. 22

Tzavara E T, Davis R J, Perry K W, Li X, Salhoff C, Bymaster F P, Witkin J M, Nomikos G G. The CB1 receptor antagonist SR141716A selectively increases monoaminergic neurotransmission in the medial prefrontal cortex: implications for therapeutic actions. Br J Pharmacol. 2003 February; 1 38(4):544-53.

Vallée M, Rivera J D, Koob G F, Purdy R H, Fitzgerald R L. Quantification of neurosteroids in rat plasma and brain following swim stress and allopregnanolone administration using negative chemical ionization gas chromatography/mass spectrometry. Anal Biochem. 2000 Dec. 1; 287(1):153-66.

Vallée M, Vitiello S, Bellocchio L, Hébert-Chatelain E, Monlezun S, Martin-Garcia E, et al. Pregnenolone can protect the brain from *cannabis* intoxication. Science. 2014 Jan. 3; 343(6166):94-8.

Volkow N. D, Baler R. D, Compton W. M, and Weiss S. R. B. Adverse health effects of marijuana use. N. Engl. J. Med. 2014 370, 2219-2227;

Walf A A and Frye C A. The use of the elevated plus maze as an assay of anxiety-related behavior in rodents. Nat Protoc. 2007; 2(2):322-8.

Wiley J L, Burston J J, Leggett D C, Alekseeva O O, Razdan R K, Mahadevan A, Martin B R. CB1 cannabinoid receptor-mediated modulation of food intake in mice. Br J Pharmacol. 2005 June; 145(3):293-300.

Wiley J L, Evans R L, Grainger D B, Nicholson K L. Age-dependent differences in sensitivity and sensitization to cannabinoids and 'club drugs' in male adolescent and adult rats. Addict Biol. 2008. 13, 277-86.

Wilson C A, Koenig J I. Social interaction and social withdrawal in rodents as readouts for investigating the negative symptoms of schizophrenia. Eur Neuropsychopharmacol. 2014; 24:759-773.

World Health Organization, The Health and Social Effects of Nonmedical *Cannabis* Use, 2016

The invention claimed is:

1. A method for treating a Cannabinoids-Related Disorder, comprising administering to a subject in need thereof a therapeutically effective amount of a compound according to Formula (I):

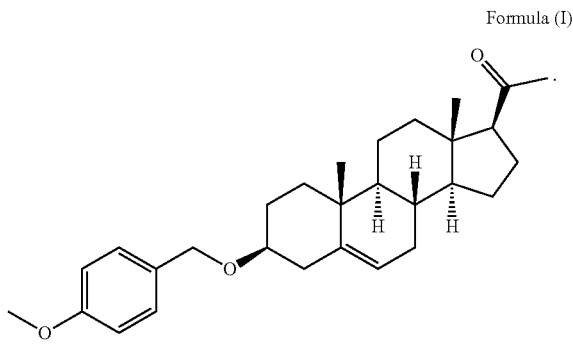

Formula (I)

2. The method of claim 1, wherein the Cannabinoids-Related Disorder is selected from the group consisting of Cannabinoids Use Disorder, Cannabinoids Intoxication, Cannabinoids Withdrawal, Other Cannabinoids-Induced Disorder, Unspecified Cannabinoids-Related Disorder, Cannabinoids Hyperemesis Syndrome, and Cannabinoids-Induced Catatonia.

3. The method of claim 2, wherein the Cannabinoids-Related Disorder is Cannabinoids Use Disorder.

4. The method of claim 2, wherein the Cannabinoids-Related Disorder is Cannabinoids Intoxication.

5. The method of claim 2, wherein the Cannabinoids-Related Disorder is Cannabinoids Withdrawal.

6. The method of claim 2, wherein the Cannabinoids-Related Disorder is an Other Cannabinoids-Induced Disorder selected from the group consisting of cannabinoids-induced anxiety disorder, cannabinoids-induced psychotic disorder, cannabinoids-induced sleep disorder, and cannabinoids intoxication delirium.

7. The method of claim 2, wherein the Cannabinoids-Related Disorder is an Unspecified Cannabinoids-Related Disorder.

8. The method of claim 2, wherein the Cannabinoids-Related Disorder is a Cannabinoids Hyperemesis Syndrome.

9. The method of claim 2, wherein the Cannabinoids-Related Disorder is a Cannabinoids-Induced Catatonia.

10. The method of claim 1, wherein the Cannabinoids-Related Disorder is a disorder associated with the use of cannabinoids derived from *Cannabis* L. plant.

11. The method of claim 1, wherein the Cannabinoids-Related Disorder is a disorder associated with the use of synthetic cannabinoids with CB1 agonist activity.

12. The method of claim 1, wherein said compound is administered to the subject via an oral route.

13. The method of claim 1, wherein said compound is administered to the subject via a parenteral route either with a ready absorbable formulation or a depot-type formulation.

14. The method of claim 1, wherein said compound is administered intravenously, subcutaneously, or intramuscularly.

15. The method of claim 1, wherein said compound is administered intranasally, by inhalation, sublingually, topically, transdermally, or in the form of a suppository or pessary.

16. The method of claim 1, wherein said compound is administered to the subject at a dose between 1 µg to 1000 mg.

17. The method of claim 1, wherein said compound is administered in an oleaginous vehicle.

18. The method of claim 17, wherein the oleaginous vehicle is a long chain triglyceride vegetable oil.

19. The method of claim 18, wherein the long chain triglyceride vegetable oil is corn oil.

\* \* \* \* \*